United States Patent
Chen et al.

(10) Patent No.: US 10,508,129 B2
(45) Date of Patent: *Dec. 17, 2019

(54) PHARMACEUTICAL TARGETING OF A MAMMALIAN CYCLIC DI-NUCLEOTIDE SIGNALING PATHWAY

(71) Applicant: Board of Regents, The University of Texas System, Austin, TX (US)

(72) Inventors: Zhijian Chen, Dallas, TX (US); Lijun Sun, Dallas, TX (US); Jiaxi Wu, Dallas, TX (US); Heping Shi, Dallas, TX (US); Chuo Chen, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/405,660

(22) Filed: May 7, 2019

(65) Prior Publication Data

US 2019/0263851 A1    Aug. 29, 2019

Related U.S. Application Data

(63) Continuation of application No. 14/653,586, filed as application No. PCT/US2013/075509 on Dec. 16, 2013, now Pat. No. 10,336,786.

(60) Provisional application No. 61/871,277, filed on Aug. 28, 2013, provisional application No. 61/829,251, filed on May 31, 2013, provisional application No. 61/739,072, filed on Dec. 19, 2012.

(51) Int. Cl.
| | |
|---|---|
| *C07H 21/02* | (2006.01) |
| *C12Q 1/6876* | (2018.01) |
| *C12Q 1/25* | (2006.01) |
| *G01N 33/573* | (2006.01) |
| *G01N 33/564* | (2006.01) |
| *A61K 31/7084* | (2006.01) |
| *A61K 39/39* | (2006.01) |
| *A61K 39/00* | (2006.01) |

(52) U.S. Cl.
CPC ......... *C07H 21/02* (2013.01); *A61K 31/7084* (2013.01); *A61K 39/39* (2013.01); *C12Q 1/25* (2013.01); *C12Q 1/6876* (2013.01); *G01N 33/564* (2013.01); *G01N 33/573* (2013.01); *A61K 2039/55511* (2013.01); *C12Q 2600/158* (2013.01); *G01N 2333/9015* (2013.01); *G01N 2333/9125* (2013.01); *G01N 2400/00* (2013.01); *G01N 2500/02* (2013.01)

(58) Field of Classification Search
CPC .............. C07H 21/02; A61K 31/7084
USPC ..................... 536/23.1; 435/6.11
See application file for complete search history.

(56) References Cited

U.S. PATENT DOCUMENTS

| | | |
|---|---|---|
| 8,367,716 B2 | 2/2013 | Karaolis |
| 9,770,467 B2 | 9/2017 | Dubensky, Jr. |
| 9,840,533 B2 | 12/2017 | Patel |
| 2006/0040887 A1 | 2/2006 | Karaolis |
| 2008/0286296 A1 | 11/2008 | Ebensen |
| 2011/0262485 A1 | 10/2011 | Barber |
| 2012/0164107 A1 | 6/2012 | Portnoy |
| 2013/0266612 A1 | 10/2013 | Fukasaka |
| 2014/0205653 A1 | 7/2014 | Dubensky, Jr. |
| 2014/0329889 A1 | 11/2014 | Vance |
| 2014/0341976 A1 | 11/2014 | Dubensky, Jr. |
| 2015/0010613 A1 | 1/2015 | Dubensky et al. |
| 2016/0210400 A1 | 7/2016 | Patel |

FOREIGN PATENT DOCUMENTS

| | | |
|---|---|---|
| WO | WO-2005/087238 A2 | 4/2005 |
| WO | WO-2005/030186 A2 | 9/2005 |
| WO | WO-2007/054279 A1 | 5/2007 |
| WO | WO-2010/017248 A2 | 2/2010 |
| WO | WO-2013/166000 A1 | 11/2013 |
| WO | WO-2013/185052 A1 | 12/2013 |
| WO | WO-2014/093936 A1 | 6/2014 |
| WO | WO-2014/179335 A1 | 11/2014 |
| WO | WO-2014/179760 A1 | 11/2014 |

OTHER PUBLICATIONS

"SciBX: Science-Business eXchange," from the makers of BioCentury and Nature, vol. 6, No. 40, Oct. 17, 2013.
Ablasser et al. 2013 "cGAS produces a 2'-5'-linked cyclic dinucleotide second messenger that activates STING," Nature 498(7454):380-384.
Barber 2011 "Cytoplasmic DNA innate immune pathways," Immunological Reviews 243(1):99-108.
Burdette et al. 2011 "STING is a direct innate immune sensor of cyclic di-GMP,", Nature 478(7370): 515-518.
Chen et al. 2010 "The potential of 3',5'-cyclic diguanylic acid (c-di-GMP) as an effective vaccine adjuvant," Vaccine 28:3080-3085.
Chiu et al. 2009 "RNA polymerise III detects cytosolic DNA and induces type I interferons through the RIG-I pathway," Cell 138(3):576-591.
Davies et al. 2012 "Coordinated regulation of accessory genetic elements produces cyclic di-nucleotides for V. cholera virulence," Cell, 149(2):358-370.
Desmet and Ishii 2012 "Nucleic acid sensing at the interface between innate and adaptive immunity invaccination," *Nat Rev Immunol.*, 12(7):479-491.
Diner et al. 2013 "The Innate Immune DNA Sensor cGAS Produces a Noncanonical Cyclic Dinucleotide that Activates Human STING," Cell Rep 3(5):1355-1361.
Ebensen et al. 2011 "Bis-(3',5')-cyclic dimeric adenosine monophosphate: strong Th1/Th2/Th17 promoting mucosal adjuvant," Vaccine 29(32):5210-5220.

(Continued)

*Primary Examiner* — Jezia Riley
(74) *Attorney, Agent, or Firm* — Dechert LLP

(57) ABSTRACT

Cyclic-GMP-AMP synthase (cGAS) and cyclic-GMP-AMP (cGAMP), including 2'3-cGAMP, 2'2-cGAMP, 3'2'-cGAMP and 3'3'-GAMP, are used in pharmaceutical formulations (including vaccine adjuvants), drug screens, therapies, and diagnostics.

15 Claims, No Drawings

(56) References Cited

OTHER PUBLICATIONS

European Search Report for Application EP 13863990.1 [EP2934598] dated Sep. 16, 2016.
Gao et al. 2013 "Cyclic [G(21,51)pA(31,51)p] Is the Metazoan Second Messenger Produced by DNA-Activated Cyclic GMP-AMP Synthase," Cell, 153:1094-1107.
Gao et al. 2013 "Cyclic GMP-AMP synthase is an innate immune sensor of HIV and other retroviruses," Science, 341:903-906, and Supplementary Materials, 18 pages.
Huang et al. 2012 "The structural basis for the sensing and binding of cyclic di-GMP by STING," Nature Structural & Molecular Biology, 19:728-730.
International Search Report for International Application No. PCT/US2013/075509 [WO/2014/099824] dated Apr. 23, 2014.
Li et al. 2013 "Pivotal roles of cGAS-cGAMP signaling in antiviral defense and immune adjuvant effects," *Science*, 341:1390-1394.
Ouyang et al. 2012 "Structural analysis of the STING adaptor protein reveals a hydrophobic dimer interface and mode of cyclic di-GMP binding," Immunity, 36:1073-1086.
Pedersen et al. 2011 "Evaluation of the sublingual route for administration of influenza H5N1 virosomes in combination with the bacterial second messenger c-di-GMP," PLoS ONE, 6(11):e26973.
Schoggins et al. 2011 "A diverse range of gene products are effectors of the type I interferon antiviral response" Nature 472:481.
Shang et al. 2012 "Crystal structures of STING protein reveal basis for recognition of cyclic di-GMP," Nature Structural & Molecular Biology 19(7):725-727.
Shu et al. 2012 "Structure of STING bound to cyclic di-GMP reveals the mechanism of cyclic dinucleotide recognition by the immune system" Nature Structural & Molecular Biology 19:722-724.
Shanahan et al. 2013 "Identification of c-di-GMP derivatives resistant to an EAL domain phosphodiesterase," Biochemistry 52(2): 365-377.
Sun et al. 2013 "Cyclic GMP-AMP Synthase Is a Cytosolic DNA Sensor That Activates the Type I Interferon Pathway," Science 339, 786-791.
Woodward et al. 2010 "c-di-AMP secreted by intracellular Listeria monocytogenes activates a host type I interferon response," Science, 328:1703-1705.
Wu et al. 2013 "Cyclic GMP-AMP Is an Endogenous Second Messenger in Innate Immune Signaling by Cytosolic DNA" Science 339, 826-830.
Yin et al. 2012 "Cyclic di-GMP sensing via the innate immune signaling protein STING," Molecular Cell, 46:735-745.
Zhang, Xu et al. 2013 "Cyclic GMP-AMP Containing Mixed Phosphodiester Linkages Is An Endogenous High-Affinity Ligand for STING," Mol Cell 51, 226-235.
Baneyx, F. 1999 "Recombinant protein expression in *Escherichia coli*," Current Opinion in Biotechnology 10:411-421.
Butt, TR et al. 2005 "SUMO fusion technology for difficult-to-express proteins," Protein Expression and Purification 43:1-9.
Einhauer, A. et al. 2001 "The FLAG peptide, a versatile fusion tag for the purification of recombinant proteins," J Biochem Biophys Methods 49:455-465.
Hoenicka, M. et al. 1999 "Purified soluble guanylyl cyckase expressed in a baculovirus/Sf9 system: stimulation by YC-1, nitric oxide,, and carbon monoxide," J Mol Med 77:14-23.
Ishihara, Y. et al. 2009 "Effect of cycil bis(3-5')diguanylic acid and its analogs on bacterial biofilm formation," FEMS Microbiol Lett 301:193-200.
The GenBank accession number for human cGAS sequence is KC294566 (Apr. 3, 2013). https://urldefense.proofpoint.com/v2/url?u=https-3A_www.ncbi.nlm.nih.gov_genbank_&d=DwlBAg&c=XHgqDMffAkUKcWD9ZTAffA&r=arp412zvR3fiu4iVHwd_wGqxtr85Js12zdtkLno9mc&m=MB_qbErsTcrsljFxGV1iHZg6N7Y3OmgTspDhf2pan5c&s=KrvaCt6vmyRMqeG2TNXEFXHnlKWsll_mfeR4WhRTLgNg&e= accessed Feb. 8, 2019.
The GenBank accession number for mouse cGAS sequence is KC294567 (Apr. 3, 2013). https://urldefense.proofpoint.com/v2/url?u=https-3A_www.ncbi.nlm.nih.gov_genbank_&&d=DwlBAg&c=XHgqDMffAkUKcWDgZTAffA&r=arp412zvR3fiu4iVHwd_wGqxtr85fJs12zdtkLno9mc&m=MB_qbErsTcrsljFxGV1iHZg6N7Y3OmgTspDhf2pan5c&s=KrvaCt6vmyRMqeG2TNXEFXHnlKWsll_mfeR4WhRTLgNg&e= Accessed Feb. 8, 2019.
Keating, S.E. et al., 2011 Cytosolic DNA sensors regulating type I interferon induction. Trends in immunology 32 (12):574-581.
Kuchta et al. 2009 Comprehensive classification of nucleotidyltransferase fold proteins: identification of novel families and their representatives in human. Nucleic Acids Res 37(22):7701-7714.
O'Neill, L. A. 2009 DNA makes RNA makes innate immunity. Cell 138(3):428-430.
Pascual et al. 2006 Systemic lupus erythematosus: all roads lead to type I interferons. Current opinion in immunology 18(6) 676-682.
Pei et al. 2008 PROMALS3D: a tool for multiple protein sequence and structure alignments. Nucleic Acids Res 36(7) 2295-2300.
Pesavento and Hengge 2009 Bacterial nucleotide-based second messengers. Curr Opin Microbiol 12(2):170-176.
Rigby et al. 2008 Nucleic acid-mediated inflammatory diseases. Bioassays 30:833-842.
Sharma, S. et al. 2011 Innate immune recognition of an AT-rich stem-loop DNA motif in the Plasmodium falciparum genome. Immunity 35(2)194-207.
Takaoka, A. et al. 2007 DAI (DLM-1/ZBP1) is a cytosolic DNA sensor and an activator of innate immune response. Nature 448:501-505.
Thomas, P. et al. 2005 "FIEK293 cell line: A vehicle for the expression of recombinant proteins," Journal of Pharmacological and Toxicological Methods 51:187-200.
Unterholzner et al. 2010 IF116 is an innate immune sensor for intracellular DNA. Nat Immunol 11(11):997-1004.
Yan and Chen 2012 Intrinsic antiviral immunity. Nat Immunol 13(3):214-222.
Yao et al. 2012 Type I Interferons in Sjogren's Syndrome. Autoimmunity reviews 12(5):5558-566.
Zhang et al. 2011 The helicase DDX4I senses intracellular DNA mediated by the adaptor STING in dendritic cells. Nat Immunol 12(10):959-965.

PHARMACEUTICAL TARGETING OF A MAMMALIAN CYCLIC DI-NUCLEOTIDE SIGNALING PATHWAY

CROSS-REFERENCE TO RELATED APPLICATIONS

This application is a continuation of application Ser. No. 14/653,586 (filed Jun. 18, 2015), which is a national phase application under 35 U.S.C. § 371 of International Application No. PCT/US2013/075509 (filed Dec. 16, 2013), which claims benefit of provisional application Nos. 61/739,072 (filed Dec. 19, 2012); 61/829,251 (filed May 31, 2013); and 61/871,277 (filed Aug. 28, 2013). The entire text of each of the above priority documents is specifically incorporated herein by reference.

This invention was made with government support under Grant Numbers ROI AI-093967 awarded by the National Institutes of Health (NIH). The government has certain rights in the invention.

INTRODUCTION

Cytosolic DNA induces type-I interferons and other cytokines that are important for antimicrobial defense but can also result in autoimmunity. This DNA signaling pathway requires the adaptor protein STING and the transcription factor IRF3, but the mechanism of DNA sensing is unclear. Here we report that mammalian cytosolic extracts synthesized cyclic-GMP-AMP (cGAMP) in vitro from ATP and GTP in the presence of DNA but not RNA. DNA transfection or DNA virus infection of mammalian cells also triggered cGAMP production. cGAMP bound to STING, leading to the activation of IRF3 and induction of interferon-$\beta$ (IFN$\beta$). Thus, cGAMP represents the first cyclic di-nucleotide in metazoa and it functions as an endogenous second messenger that triggers interferon production in response to cytosolic DNA.

Through biochemical fractionation and quantitative mass spectrometry, we also identified a cGAMP synthase (cGAS), which belongs to the nucleotidyltransferase family. Overexpression of cGAS activated the transcription factor IRF3 and induced IFN$\beta$ in a STING-dependent manner. Knockdown of cGAS inhibited IRF3 activation and IFN$\beta$ induction by DNA transfection or DNA virus infection. cGAS bound to DNA in the cytoplasm and catalyzed cGAMP synthesis. These results indicate that cGAS is a cytosolic DNA sensor that induces interferons by producing the second messenger cGAMP.

The invention applies these findings to novel methods and composition relating to cyclic-GMP-AMP synthase (cGAS) and cyclic-GMP-AMP (cGAMP), including their use in formulations (including vaccine adjuvants), drug screens, therapies, and diagnostics.

SUMMARY

In one aspect the invention provides cell-based drug screens including methods of inhibiting cGAS, comprising contacting a cell or cell extract with an effective amount of an exogenous cGAS inhibitor, and detecting a resultant inhibition of the synthase. In particular embodiments the resultant inhibition is detected inferentially by cyclic-GMP-AMP-induced IRF3 activation (dimerization or nuclear translocation), interferon production, or NF-kB activation.

In another aspect the invention provides therapies including methods of inhibiting cGAS, comprising contacting a cell determined to be in need thereof with an effective amount of an exogenous cGAS inhibitor. In particular embodiments the method comprises administering the inhibitor to a mammal determined to be in need thereof and comprising the cell, and/or the inhibitor is a small-molecule cyclase inhibitor or is a cGAS-specific shRNA or siRNA.

In another aspect the invention provides in vitro drug screens including methods of inhibiting cGAS, comprising contacting a mixture comprising the synthase, ATP, GTP, and an inhibitor, under conditions wherein the inhibitor inhibits catalytic conversion by the synthase of the ATP and GTP to cyclic-GMP-AMP and inorganic pyrophosphate, and detecting a resultant inhibition of the synthase. In a particular embodiment mixture further comprises DNA and the conversion is DNA-dependent. In other embodiments the cGAS is constitutively active.

In another aspect the invention provides in vitro drug binding assays including methods of inhibiting cGAS binding to a substrate or cofactor, comprising contacting a mixture comprising the synthase and an ATP or GTP substrate or a DNA cofactor, and an inhibitor, under conditions wherein the inhibitor inhibits binding of the synthase to the substrate or cofactor, and detecting a resultant inhibition of the binding.

In another aspect the invention provides methods of making cGAMP comprising forming a mixture comprising the cGAS, ATP and GTP, under conditions wherein the synthase catalytic converts the ATP and GTP to cGAMP, wherein the synthase, ATP and GTP are in predefined amounts, or the method further comprises the step of isolating or detecting the resultant cGAMP. In particular embodiments the mixture further comprises DNA and the conversion is DNA-dependent.

In another aspect the invention provides methods of detecting cGAMP levels, cGAS levels or cGAS mutations comprising the step of: detecting in a sample from a person cGAMP levels, cGAS levels or cGAS mutations, and assigning to the person an autoimmune disease metric based on the cGAMP levels, cGAS levels or cGAS mutations; and optionally administering to the person a therapy for the autoimmune disease.

In another aspect the invention provides compositions comprising a predetermined amount of cGAMP, such as a vaccine further comprising an immunogen for a target pathogen, wherein the cGAMP provides an adjuvant. In particular embodiments, the composition is free of other cyclic di-nucleotides, and/or otherwise suitable as an adjuvant or vaccine, e.g. sterile, pharmaceutically acceptable, in defined, predetermined amounts, ratios, etc., and the compositions may be in bulk or unit dosages, quantified for individual usage. The invention also provides methods of inducing or promoting an immune response comprising administering to a mammal in need thereof an effective amount of such compositions. In particular embodiments, the administering is mucosal (sublingual or intranasal), intramuscular or subcutaneous.

The invention includes all combinations of the recited particular embodiments. Further embodiments and the full scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

The invention provides methods and composition relating to cGAS and cGAMP, including their use in formulations (including vaccine adjuvants), drug screens, therapies, and diagnostics.

Highlights: 2'3'-cGAMP is an endogenous second messenger produced by mammalian cells; 2'3'-cGAMP is a high affinity ligand for STING; 2'3'-cGAMP is a potent inducer of type-I interferons; 2'3'-cGAMP binding induces conformational changes of STING.

In one aspect the invention provides cell-based drug screens including methods of inhibiting cGAS, comprising contacting a cell or cell extract with an effective amount of an exogenous cGAS inhibitor, and detecting a resultant inhibition of the synthase. The synthase is typically human or murine cGAS, and may be truncated, recombined in fusion protein, or otherwise modified to suit the assay. Typically the method is practiced in as a screening assay wherein the inhibitor is a candidate inhibitor for analysis, which may be from a library, lead optimization, etc. The inhibition be detected directly or inferentially, such as by cGAMP-induced IRF3 activation (dimerization or nuclear translocation), interferon production or NF-kB activation, direct detection of cGAMP and other products by, for examples, mass spectrometry, antibody-based assays (e.g., ELISA, ALPHA, fluorescent polarization etc.). For example, IFN RNA may be measured by q-RT-PCR, and IRF3 dimerization by native gel electrophoresis. Additional suitable readouts include measurements of ATP, GTP, and pyrophosphate (PPi).

In another aspect the invention provides therapies including methods of inhibiting cGAS, comprising contacting a cell determined to be in need thereof with an effective amount of an exogenous cGAS inhibitor. In particular embodiments the method comprises administering the inhibitor to a mammal determined to be in need thereof and comprising the cell, and/or the inhibitor is a small-molecule cyclase inhibitor, or is a cGAS-specific shRNA or siRNA, or other RNAi or antisense RNA cGAS-specific inhibitor.

Our data indicate that cGAS and the cGAS-cGAMP pathway is important for triggering inflammatory responses to self and foreign DNA, and hence cGAS inhibitors can be used to reduce pathogenic cGAS activity of associated autoimmune diseases. Similarly, our data indicate that cGAS is also important for the transformation from normal to cancer cells and also for the survival and metastasis of cancer cells, and hence cGAS inhibitors can be used to reduce pathogenic cGAS activity of associated neoplastic diseases.

Current therapy for lupus and other autoimmune diseases involve massive doses of immunosuppressive agents, which have severe side effects. Although a new BAFF antibody (Benlysta) has been approved for lupus treatment, it is only marginally effective. Targeting cGAS with small molecule inhibitors, particularly orally available ones, provides significant advantages over the existing therapies. cGAS inhibitors target the root cause of lupus and other autoimmune diseases, and provide therapeutic benefits to patients. Moreover, the cytosolic DNA innate immunity pathway is aberrantly activated under autoimmune conditions such as systemic lupus erythematosus (SLE), Sjögren's syndrome, and Aicardi-Goutières syndrome, and cGAS inhibition provides a rational treatment of these and other autoimmune diseases.

In another aspect the invention provides in vitro drug screens including methods of inhibiting cGAS, comprising contacting a mixture comprising the synthase, ATP, GTP, and an inhibitor, under conditions wherein the inhibitor inhibits catalytic conversion by the synthase of the ATP and GTP to cGAMP and inorganic pyrophosphate, and detecting a resultant inhibition of the synthase. In a particular embodiment mixture further comprises DNA and the conversion is DNA-dependent. In other embodiments the cGAS is constitutively active. Typically the method is practiced in as a screening assay wherein the inhibitor is a candidate inhibitor for analysis, which may be from a library, lead optimization, etc. The mixture may be contained in cell or cell extract, or may be acellular.

In another aspect the invention provides in vitro drug binding assays including methods of inhibiting cGAS binding to a substrate or cofactor, comprising contacting a mixture comprising the synthase and an ATP or GTP substrate or a DNA cofactor, and an inhibitor, under conditions wherein the inhibitor inhibits binding of the synthase to the substrate or cofactor, and detecting a resultant inhibition of the binding. Typically the method is practiced in as a screening assay wherein the inhibitor is a candidate inhibitor for analysis, and may be implemented in variety of suitable formats including solid phase immune assays, fluorescent polarization assays, etc.

In another aspect the invention provides methods of making cGAMP comprising forming a mixture comprising the cGAS, ATP and GTP, under conditions wherein the synthase catalytic converts the ATP and GTP to cGAMP, wherein the synthase, ATP and GTP are in predefined amounts, or the method further comprises the step of isolating or detecting the resultant cGAMP. In particular embodiments the mixture further comprises DNA and the conversion is DNA-dependent.

Pathogenic expression of cGAS activity, particularly as a result of over-expression or mutation is associated with human autoimmune diseases; hence, the invention also provides methods and assays for detecting cGAS levels or mutations, particularly as a diagnostic tool for human autoimmune diseases. Accordingly, in another aspect the invention provides methods of detecting cGAMP levels, cGAS levels or cGAS mutations comprising the step of: detecting in a sample from a person cGAMP levels, cGAS levels or cGAS mutations, and assigning to the person an autoimmune disease metric based on the cGAMP levels, cGAS levels or cGAS mutations; and optionally administering to the person a therapy for the autoimmune disease.

In another aspect the invention provides compositions comprising a predetermined amount of cGAMP, such as a vaccine further comprising an immunogen for a target pathogen, wherein the cGAMP provides an adjuvant. In particular embodiments, the composition is substantially or essentially free of other cyclic di-nucleotides. The invention also provides methods of inducing or promoting an immune response comprising administering to a mammal in need thereof an effective amount of such compositions. In particular embodiments, the administering is mucosal (sublingual or intranasal), intramuscular or subcutaneous.

As a potent inducer of type-I interferons, cGAMP provides a rational immune adjuvant. cGAMP may be used as vaccine adjuvants, particularly with mucosal vaccines, and may be formulated with immunogens and delivered as have been cyclic-di-GMP and c-di-AMP as vaccine adjuvants; see, e.g. Pedersen, et al. PLoS ONE, November 2011, 6, 11, e26973; Ebensen et al., Vaccine 29, 2011, 5210-5220; Chen et al., Vaccine 28, 2010, 3080-3085. In fact the cGAMP adjuvant are often more effective because cGAMP is more potent than c-di-GMP in inducing interferons.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

Example 1

Cyclic-GMP-AMP is an Endogenous Second Messenger in Innate Immune Signaling by Cytosolic DNA Host defense against foreign genetic elements is one of the most fundamental functions of a living organism. The presence of self or foreign DNA in the cytoplasm is sensed by eukaryotic cells as a danger signal or a sign of foreign invasion (1). DNA can be introduced into the cytoplasm by bacterial or viral infection, transfection, or 'leakage' from the nucleus or mitochondria under some pathological conditions that cause autoimmune diseases such as lupus. In mammalian cells, cytosolic DNA triggers the production of type-I interferons (IFNs) and other cytokines through the endoplasmic reticulum protein STING (also known as MITA, MPYS or ERIS) (2). STING recruits and activates the cytosolic kinases IKK and TBK1, which activate the transcription factors NF-κB and IRF3, respectively. NF-κB and IRF3 then enter the nucleus and function together to induce IFNs and other cytokines. DNA-dependent RNA polymerase III has been shown to be a sensor that detects and transcribes AT-rich DNA such as poly[dA:dT] into an RNA ligand capable of stimulating the RIG-I pathway to induce IFNs (3, 4). However, most DNA sequences do not activate the RNA polymerase III-RIG-I pathway. Instead, cytosolic DNA activates the STING-dependent pathway in a sequence-independent manner. How cytosolic DNA activates the STING pathway remains elusive.

We hypothesized that DNA binds to and activates a putative cytosolic DNA sensor, which then directly or indirectly activates STING, leading to the activation of IRF3 and NF-κB. To test this model, we developed an in vitro complementation assay using the murine fibrosarcoma cell line L929, which is known to induce interferon-β (IFNβ) in a STING-dependent manner (5). We used a L929 cell line stably expressing a short hairpin (sh)RNA against STING such that DNA transfection would only activate factors upstream of STING, including the putative DNA sensor. The L929-shSTING cells were transfected with different types of DNA and then cytoplasmic extracts from these cells were mixed with the human monocytic cell line THP1 or murine macrophage cell line Raw264.7, which was permeabilized with perfringolysin O (PFO). PFO treatment pokes holes in the plasma membrane (6), allowing the cytoplasm to diffuse in and out of cells, while retaining organelles including endoplasmic reticulum (which contains STING) and Golgi apparatus inside the cells (7). If an upstream activator of STING is generated in the DNA transfected cells, the cytoplasm containing such an activator is expected to activate STING in the PFO-permeabilized cells, leading to the phosphorylation and dimerization of IRF3.

Cytoplasmic extracts from L929-shSTING cells transfected with a DNA sequence known as interferon-stimulatory DNA (ISD), poly[dA:dT], a GC-rich 50-base pair dsDNA (G:C50), poly[dI:dC] or herring testis DNA (HT-DNA) activated IRF3 in permeabilized THP1 cells, indicating that this activity was independent of DNA sequence.

To determine if the STING activator is a protein, we incubated the cytoplasmic extracts at 95° C. to denature most proteins and then incubated the 'heat supernatant' with permeabilized THP1 cells. Surprisingly, the heat supernatant from the ISD or HT DNA transfected cells caused IRF3 dimerization. This activity was resistant to treatment with Benzonase, which degrades both DNA and RNA, or proteinase K. Thus, the STING activator is probably not a protein, DNA or RNA.

To test if DNA could stimulate the generation of the heat-resistant STING activator in vitro, we incubated HT DNA with L929-shSTING cytoplasmic extracts (S100) in the presence of ATP. The reaction mixture was heated at 95° C. to denature proteins. Remarkably, incubation of the supernatant with permeabilized Raw264.7 cells led to IRF3 dimerization. This activity depended on the addition of DNA to the cytoplasmic extracts. Other DNA, including poly[dA:dT], poly[dG:dC] and ISD, also stimulated the generation of the STING activator in L929-shSTING cytoplasmic extracts, whereas poly[I:C] and single-stranded RNA had no activity. Similar results were obtained with permeabilized THP1 cells. Knockdown of STING in the permeabilized THP1 cells abolished IRF3 activation by the heat-resistant factor generated by DNA transfected into L929 cells or DNA added to L929 cytosolic extracts. Control experiments showed that the knockdown of STING inhibited the activation of IRF3 and induction of IFNβ and TNFα in THP1 cells by HT-DNA transfection, but IRF3 activation by poly[I:C] transfection or Sendai virus infection, which is known to activate the RIG-I pathway, was unaffected by the STING knockdown. We also tested cytoplasmic extracts from several cell lines for their ability to produce the heat-resistant STING activator. Incubation of HT-DNA with extracts from primary MEF cells, mouse bone marrow derived macrophages (BMDM) and L929 cells led to generation of the heat-resistant factor that activated IRF3. Human cell extracts from THP1, but not HEK293T, were also able to produce this STING activator. These results are in agreement with our previous finding that primary MEF, BMDM, L929 and THP1 cells, but not HEK293T cells, possessed the STING-dependent, RNA polymerase III-independent, pathway to induce type-I interferons (3).

We next purified the heat-resistant STING activator from L929 cell extracts using several chromatographic steps including a STING-Flag affinity purification step. Previous research has shown that the bacterial molecules cyclic-di-AMP and cyclic-di-GMP bind to STING and induce type-I interferons (8, 9). However, using nano liquid chromatography mass spectrometry (nano-LC-MS), we did not detect MS or MS/MS spectra consistent with those expected of c-di-GMP ($[M+H]^+$=691) or c-di-AMP ($[M+H]^+$=659). Interestingly, in-depth examination of the MS spectra revealed two ions with mass to charge ratios (m/z) of 675.1 ($z=1^+$) and 338.1 ($z=2^+$), which were present in the active fractions but absent in the background spectra. These m/z values, despite the low mass accuracy of the mass spectrometer (LTQ), were equivalent to the average calculated m/z values of c-di-GMP and c-di-AMP (675=[691+659]/2). This observation indicated that the detected ion was a hybrid of c-di-GMP and c-di-AMP, i.e., cyclic-GMP-AMP (m/z=675.107, $z=1^+$; m/z=338.057, $z=2^+$). Collision induced dissociation (CID) fragmentation of this ion (m/z=338.1, z=2$^+$) revealed several prominent ions with m/z values expected of the product ions of c-GMP-AMP (cGAMP). Importantly, quantitative mass spectrometry using selective reaction monitoring (SRM) showed that the abundance of the ions representing cGAMP in the fractions from a C18 column correlated very well with their IRF3-stimulatory activities. cGAMP has recently been identified in the bacterium *Vibro cholera* and shown to play a role in bacterial chemotaxis and colonization (10). However, cGAMP has not been reported to exist or function in eukaryotic cells.

To verify the identity of the heat resistant STING activator, we used a high-resolution high-accuracy mass spectrometer (Q Exactive, Thermo) to perform nano-LC-MS analysis. The cell-derived STING activator had m/z of 675.107 (z=1$^+$) and 338.057 (z=2$^+$), which exactly matched the theoretical values of cGAMP. To further characterize the structure and function of cGAMP, we developed a ten-step single-flask protocol to chemically synthesize cGAMP. The MS/MS spectra of the cell-derived STING activator were identical to those of the chemically synthesized cGAMP. These results demonstrate that L929 cells produced cGAMP.

Quantitative RT-PCR and ELISA assays showed that chemically synthesized cGAMP induced IFNβ RNA and protein in L929 cells after introduction into the cells. Titration experiments showed that cGAMP induced IFNβ RNA robustly even at concentrations as low as 10 nM. In fact, cGAMP was much more potent than c-di-GMP in inducing IFNβ based on ELISA assays. cGAMP was also more potent than c-di-GMP and c-di-AMP in activating IRF3. To determine if L929 extracts contained enzymes that could synthesize other types of di-nucleotides or oligonucleotides capable of activating IRF3, we tested all four ribonucleotides in various combinations. ATP and GTP were both necessary and sufficient to support the synthesis of an activator of IRF3, further supporting that L929 contained an enzyme that synthesizes cGAMP from ATP and GTP.

To determine if DNA virus infection leads to the production of cGAMP in cells, we infected L929 cells with HSV-1 lacking ICP34.5, a viral protein known to antagonize interferon production in the infected cells (11). Like DNA transfection, HSV-1ΔICP34.5 infection led to IRF3 activation in L929 cells. Cell extracts from the DNA-transfected or virus-infected cells contained a heat-resistant factor that could activate IRF3 in permeabilized Raw264.7 cells. As a control, we infected L929 cells with a vesicular stomatitis virus strain, VSV-ΔM51-GFP, an RNA virus known to trigger strong interferon production through the RIG-I pathway (12, 13). In contrast to HSV-1, VSV-infected cells did not contain the heat-resistant IRF3 activator in the same in vitro assay, although VSV infection did induce IRF3 activation in L929 cells. The heat resistant factor in HSV-1 infected cells was enriched by reverse phase HPLC and quantified by nano-LC-MS using SRM. DNA transfected or HSV-1 infected cells, but not mock treated or VSV infected cells, produced elevated levels of cGAMP. Kinetic experiments showed that, after DNA was transfected into L929 cells, cGAMP was produced before IRF3 dimerization, and IFNβ induction could be detected. To test if DNA viruses could induce cGAMP production in human cells, we infected THP1 cells with HSV1 or Vaccinia virus (VACV). Both viruses induced IRF3 dimerization in the cells. Importantly, both viruses also triggered the production of cGAMP that activated IRF3. Collectively, these results indicate that DNA transfection and DNA virus infections in human and mouse cells produced cGAMP, which led to IRF3 activation.

To determine if cGAMP activates IRF3 through STING, we carried out three sets of experiments. First, we established a HEK293T cell line stably expressing STING, stimulated these cells with cGAMP and then measured IFNβ induction by quantitative RT-PCR. HEK293T cells did not respond to cGAMP, likely due to a lack of or a very low level of STING expression in these cells. The expression of STING in HEK293T cells rendered a high level of IFNβ induction by cGAMP. However, DNA did not stimulate HEK293T/STING cells to induce IFNβ, consistent with a defect of HEK293T cells in producing cGAMP in response to DNA stimulation. In contrast, L929 cells induced IFNβ in response to stimulation by either cGAMP or DNA. HSV-1 infection induced IRF3 dimerization in L929, but not HEK293T or HEK29T/STING cells, indicating that the production of cGAMP is important for HSV-1 to activate IRF3 in cells. Indeed, extracts from HSV1-infected L929, but not from HEK293T or HEK293T/STING cells, contained the cGAMP activity that led to IRF3 dimerization in permeabilized Raw264.7 cells. These results indicate that the expression of STING in HEK293T cells installed the ability of the cells to activate IRF3 and induce IFNβ in response to cGAMP, but was insufficient to install the response to DNA or DNA viruses due to a defect of HEK293T cells in synthesizing cGAMP.

Second, we tested the response of L929 and L929-shSTING cells to cGAMP. Similar to ISD and c-di-GMP, cGAMP-induced IRF3 dimerization was dependent on STING. In contrast, poly[I:C] still induced IRF3 dimerization in the absence of STING. These results demonstrate that STING is necessary for cGAMP to activate IRF3.

Finally, we examined whether STING binds to cGAMP directly. Recombinant STING protein containing residues 139-379, which has been shown to bind c-di-GMP (14), was expressed and purified from *E. coli* and then incubated with $^{32}$P-cGAMP followed by UV-induced crosslinking. A radiolabelled band corresponding to cross-linked STING-cGAMP complex was detected when both STING and $^{32}$P-cGAMP were present. High concentrations of ATP or GTP did not compete with the formation of STING-cGAMP complex. By contrast, the intensity of this band decreased as the concentrations of competing cold cGAMP, c-di-GMP or c-di-AMP increased, indicating that the cGAMP binding sites on STING overlap with those that interact with c-di-GMP and c-di-AMP. Indeed, mutations of several residues that were recently shown to participate in the binding of STING to c-di-GMP (14), including S161Y, Y240S and N242A, also impaired the binding of STING to cGAMP. Collectively, these results demonstrate that cGAMP is a ligand that binds to and activates STING.

Cyclic di-nucleotides have been shown to function as bacterial second messengers that regulate a variety of physiological processes, including bacterial motility and biofilm formation (15). A recent report showed that c-di-GMP is produced in the protozoan *Dictyostelium* and functions as a morphogen to induce stalk cell differentiation (16). In this example, we identified cGAMP as the first cyclic di-nucleotide in metazoa. Moreover, we showed that cGAMP is a potent inducer of type-I interferons. The role of cGAMP is similar to that of cAMP, the best-studied second messenger (17). Like cAMP, which is synthesized by adenylate cyclase upon its activation by upstream ligands, cGAMP is synthesized by a cyclase in response to stimulation by a DNA ligand (18). cAMP binds to and activates protein kinase A and other effector molecules. Similarly, cGAMP binds to and activates STING to trigger the downstream signaling cascades. As an endogenous molecule in mammalian cells, cGAMP may be used in immune therapy or as a vaccine adjuvant.

REFERENCES AND NOTES

1. R. Barbalat, S. E. Ewald, M. L. Mouchess, G. M. Barton, Nucleic Acid Recognition by the Innate Immune System. *Annu Rev Immunol*, (April 5).
2. G. N. Barber, Cytoplasmic DNA innate immune pathways. *Immunological reviews* 243, 99 (September, 2011).
3. Y. H. Chiu, J. B. Macmillan, Z. J. Chen, RNA polymerase III detects cytosolic DNA and induces type I interferons through the RIG-I pathway. *Cell* 138, 576 (Aug. 7, 2009).
4. A. Ablasser et al., RIG-I-dependent sensing of poly(dA:dT) through the induction of an RNA polymerase III-transcribed RNA intermediate. *Nat Immunol*, (Jul. 16, 2009).
5. Y. Tanaka, Z. J. Chen, STING Specifies IRF3 Phosphorylation by TBK1 in the Cytosolic DNA Signaling Pathway. *Sci Signal* 5, ra20 (2012).
6. J. Rossjohn et al., Structures of perfringolysin O suggest a pathway for activation of cholesterol-dependent cytolysins. *Journal of molecular biology* 367, 1227 (Apr. 13, 2007).
7. T. Saitoh et al., Atg9a controls dsDNA-driven dynamic translocation of STING and the innate immune response. *Proceedings of the National Academy of Sciences of the United States of America* 106, 20842 (Dec. 8, 2009).
8. J. J. Woodward, A. T. Iavarone, D. A. Portnoy, c-di-AMP secreted by intracellular Listeria monocytogenes activates a host type I interferon response. *Science* 328, 1703 (Jun. 25, 2010).
9. D. L. Burdette et al., STING is a direct innate immune sensor of cyclic di-GMP. *Nature* 478, 515 (Oct. 27, 2011).
10. B. W. Davies, R. W. Bogard, T. S. Young, J. J. Mekalanos, Coordinated regulation of accessory genetic elements produces cyclic di-nucleotides for *V. cholerae* virulence. *Cell* 149, 358 (Apr. 13, 2012).
11. K. L. Mossman, J. R. Smiley, Herpes simplex virus ICP0 and ICP34.5 counteract distinct interferon-induced barriers to virus replication. *Journal of virology* 76, 1995 (February, 2002).
12. D. F. Stojdl et al., VSV strains with defects in their ability to shutdown innate immunity are potent systemic anti-cancer agents. *Cancer Cell* 4, 263 (October, 2003).
13. Q. Sun et al., The specific and essential role of MAVS in antiviral innate immune responses. *Immunity* 24, 633 (May, 2006).
14. Q. Yin et al., Cyclic di-GMP sensing via the innate immune signaling protein STING. *Molecular cell* 46, 735 (Jun. 29, 2012).
15. C. Pesavento, R. Hengge, Bacterial nucleotide-based second messengers. *Curr Opin Microbiol* 12, 170 (April, 2009).
16. Z. H. Chen, P. Schaap, The prokaryote messenger c-di-GMP triggers stalk cell differentiation in *Dictyostelium*. *Nature* 488, 680 (Aug. 30, 2012).
17. S. A. Blumenthal, Earl Sutherland (1915-1975) and the discovery of cyclic AMP. *Perspect Biol Med* 55, 236 (2012).
18. L. Sun, J. Wu, F. Du, X. Chen, Z. J. Chen, Cyclic GMP-AMP synthase is a cytosolic DNA sensor that activates the type-I interferon pathway. Science, (2012).

Example 2

Cyclic GMP-AMP Synthase is a Cytosolic DNA Sensor that Activates the Type-I Interferon Pathway DNA was known to stimulate immune responses long before it was shown to be a genetic material, but the mechanism by which DNA functions as an immune stimulant remains poorly understood (1). Although DNA can stimulate the production of type-I interferons in dendritic cells through binding to Toll-like receptor 9 (TLR9) in the endosome, how DNA in the cytosol induces IFN is still unclear. In particular, the sensor that detects cytosolic DNA in the interferon pathway remains elusive (2). Although several proteins, including DAI, RNA polymerase III, IFI16, DDX41 and several other DNA helicases, have been suggested to function as the potential DNA sensors that induce IFN, none has been met with universal acceptance (3).

Purification and Identification of Cyclic GMP-AMP Synthase (cGAS).

We showed that delivery of DNA to mammalian cells or cytosolic extracts triggered the production of cyclic GMP-AMP (cGAMP), which bound to and activated STING, leading to the activation of IRF3 and induction of IFNβ (4). To identify the cGAMP synthase (cGAS), we fractionated cytosolic extracts (S100) from the murine fibrosarcoma cell line L929, which contains the cGAMP synthesizing activity. This activity was assayed by incubating the column fractions with ATP and GTP in the presence of herring testis DNA (HT-DNA). After digesting the DNA with Benzonase and heating at 95° C. to denature proteins, the heat-resistant supernatants that contained cGAMP were incubated with Perfringolysin O (PFO)-permeabilized Raw264.7 cells (transformed mouse macrophages). cGAMP-induced IRF3 dimerization in these cells were analyzed by native gel electrophoresis (4). Using this assay, we carried out three independent routes of purification, each consisting of four steps of chromatography but differing in the columns or the order of the columns that were used. In particular, the third route included an affinity purification step using a biotinylated DNA oligo (a 45-bp DNA known as Immune Stimulatory DNA or ISD). We estimated that we achieved a range of 8000-15,000 fold purification and 2-5% recovery of the activity from these routes of fractionation. However, in the last step of each of these purification routes, silver staining of the fractions did not reveal clear protein bands that co-purified with the cGAS activity, suggesting that the abundance of the putative cGAS protein might be very low in L929 cytosolic extracts.

We developed a quantitative mass spectrometry strategy to identify a list of proteins that co-purified with the cGAS activity at the last step of each purification route. We reasoned that the putative cGAS protein must co-purify with its activity in all three purification routes, whereas most 'contaminating' proteins would not. Thus, from the last step of each purification route, we chose fractions that contained most of the cGAS activity (peak fractions) and adjacent fractions that contained very weak or no activity. The proteins in each fraction were separated by SDS-PAGE and identified by nano liquid chromatography mass spectrometry (nano-LC-MS). The data were analyzed by label-free quantification using the MaxQuant software (5). Remarkably, although many proteins co-purified with the cGAS activity in one or two purification routes, only three proteins co-purified in all three routes. All three were putative uncharacterized proteins: E330016A19 (accession #: NP_775562), Arf-GAP with dual PH domain-containing protein 2 (NP_742145) and signal recognition particle 9 kDa protein (NP_036188). Among these, more than 24 unique peptides were identified in E330016A19, representing 41% coverage of this protein of 507 amino acids.

Bioinformatic analysis drew our attention to E330016A19, which exhibited structural and sequence homology to the catalytic domain of oligoadenylate synthase (OAS1). In particular, E330016A19 contains a conserved G[G/S]$x_{9-13}$[E/D]h[E/D]h motif, where $X_{9-13}$ indicates 9-13 flanking residues consisting of any amino acid and h indicates a hydrophobic amino acid. This motif is found in the nucleotidyltransferase (NTase) family (6). Besides OAS1, this family includes adenylate cyclase, poly[A] polymerase and DNA polymerases. The C-terminus of E330016A19 contained a Male Abnormal 21 (Mab21) domain, which was first identified in the *C. elegans* protein Mab21 (7). Sequence alignment revealed that the C-terminal NTase and Mab21 domains are highly conserved from zebrafish to human, whereas the N-terminal sequences are much less conserved (8). Interestingly, the human homologue of E330016A19, C6orf150 (also known as MB21D1) was recently identified as one of several positive hits in a screen for interferon-stimulated genes (ISGs) whose overexpression inhibited viral replication (9). For clarity and on the basis of evidence presented in this paper, we propose to name the mouse protein E330016A19 as m-cGAS and the human homologue C6orf150 as h-cGAS. Quantitative RT-PCR showed that the expression of m-cGAS was low in immortalized MEF cells but high in L929, Raw264.7 and bone marrow-derived macrophages (BMDM). Similarly, the expression of h-cGAS RNA was very low in HEK293T cells but high in the human monocytic cell line THP1. Immunoblotting further confirmed that h-cGAS protein was expressed in THP1 but not HEK293T cells. Thus, the expression levels of m-cGAS and h-cGAS in different cell lines correlated with the ability of these cells to produce cGAMP and induce IFNβ in response to cytosolic DNA (4, 10).

Catalysis by cGAS Triggers Type-I Interferon Production.

Overexpression of m-cGAS in HEK293T, which lacks STING expression, did not induce IFNβ, whereas stable expression of STING in HEK293T cells rendered these cells highly competent in IFNβ induction by m-cGAS. Importantly, point mutations of the putative catalytic residues G198 and S199 to alanine abolished the ability of m-cGAS to induce IFNβ. These mutations, as well as mutations of the other putative catalytic residues E211 and D213 to alanine, also abrogated the ability of m-cGAS to induce IRF3 dimerization in HEK293T-STING cells. The magnitude of IFNβ induction by c-GAS was comparable to that induced by MAVS (an adaptor protein that functions downstream of the RNA sensor RIG-I) and was several orders higher than those induced by other putative DNA sensors, including DAI, IFI16 and DDX41. To determine if overexpression of cGAS and other putative DNA sensors led to the production of cGAMP in cells, supernatants from heat-treated cell extracts were incubated with PFO-permeabilized Raw264.7 cells, followed by measurement of IRF3 dimerization. Among all the proteins expressed in HEK293T-STING cells, only cGAS was capable of producing the cGAMP activity in the cells.

To test if cGAS could synthesize cGAMP in vitro, we purified wild-type (WT) and mutant Flag-cGAS proteins from transfected HEK293T cells. WT m-cGAS and h-cGAS, but not the catalytically inactive mutants of cGAS, were able to produce the cGAMP activity, which stimulated IRF3 dimerization in permeabilized Raw264.7 cells. Importantly, the in vitro activities of both m-cGAS and h-cGAS were dependent on the presence of HT-DNA. To test if DNA enhances IFNβ induction by cGAS in cells, different amounts of cGAS expression plasmid was transfected with or without HT-DNA into HEK293T-STING cells. HT-DNA significantly enhanced IFNβ induction by low (10 and 50 ng) but not high (200 ng) doses of cGAS plasmid. In contrast to cGAS, IFI16 and DDX41 did not induce IFNβ even when HT-DNA was co-transfected.

cGAS is Required for IFNβ Induction by DNA Transfection and DNA Virus Infection.

We used two different pairs of siRNA to knock down m-cGAS in L929 cells, and found that both siRNA oligos significantly inhibited IFNβ induction by HT-DNA, and that the degree of inhibition correlated with the efficiency of knocking down m-cGAS RNA. We also established two L929 cell lines stably expressing shRNA sequences targeting distinct regions of m-cGAS. The ability of these cells to induce IFNβ in response to HT-DNA was severely compromised as compared to another cell line expressing a control shRNA (GFP). Importantly, expression of cGAS in the L929-sh-cGAS cells restored IFNβ induction. Expression of STING or MAVS in L929-sh-cGAS cells or delivery of cGAMP to these cells also induced IFNβ. In contrast, expression of cGAS or delivery of cGAMP failed to induce IFNβ in L929-shSTING cells, whereas expression of STING or MAVS restored IFNβ induction in these cells. Quantitative RT-PCR analyses confirmed the specificity and efficiency of knocking down cGAS and STING in the L929 cell lines stably expressing the corresponding shRNAs. These results indicate that cGAS functions upstream of STING and is required for IFNβ induction by cytosolic DNA.

Herpes simplex virus 1 (HSV-1) is a DNA virus known to induce IFNs through the activation of STING and IRF3 (3). Importantly, shRNA against m-cGAS, but not GFP, in L929 cells strongly inhibited IRF3 dimerization induced by HSV-1 infection. In contrast, knockdown of cGAS did not affect IRF3 activation by Sendai virus, an RNA virus. To determine if cGAS is required for the generation of cGAMP in cells, we transfected HT-DNA into L929-shGFP and L929-sh-cGAS or infected these cells with HSV-1, then prepared heat-resistant fractions that contained cGAMP, which was subsequently delivered to permeabilized Raw264.7 cells to measure IRF3 activation. Knockdown of cGAS largely abolished the cGAMP activity generated by DNA transfection or HSV-1 infection. Quantitative mass spectrometry using selective reaction monitoring (SRM) showed that the abundance of cGAMP induced by DNA transfection or HSV-1 infection was markedly reduced in L929 cells depleted of cGAS. Taken together, these results demonstrate that cGAS is essential for producing cGAMP and activating IRF3 in response to DNA transfection or HSV-1 infection.

To determine if cGAS is important in the DNA sensing pathway in human cells, we established a THP1 cell line stably expressing a shRNA targeting h-cGAS. The knockdown of h-cGAS strongly inhibited IFNβ induction by HT-DNA transfection or infection by vaccinia virus, another DNA virus, but not Sendai virus. The knockdown of h-cGAS also inhibited IRF3 dimerization induced by HSV-1 infection in THP1 cells. This result was further confirmed in another THP1 cell line expressing a shRNA targeting a different region of h-cGAS. The strong and specific effects of multiple cGAS shRNA sequences in inhibiting DNA-induced IRF3 activation and IFNβ induction in both mouse and human cell lines demonstrate a key role of cGAS in the STING-dependent DNA sensing pathway.

Recombinant cGAS Protein Catalyzes cGAMP Synthesis from ATP and GTP in a DNA-Dependent Manner.

To test if cGAS is sufficient to catalyze cGAMP synthesis, we expressed Flag-tagged h-cGAS in HEK293T cells and purified it to apparent homogeneity. In the presence of HT-DNA, purified c-GAS protein catalyzed the production of cGAMP activity, which stimulated IRF3 dimerization in permeabilized Raw264.7 cells. DNase-I treatment abolished this activity. The cGAS activity was also stimulated by other DNA, including poly(dA:dT), poly(dG:dC) and ISD, but not the RNA poly(I:C). The synthesis of cGAMP by cGAS required both ATP and GTP, but not CTP or UTP. These results indicate that the cyclase activity of purified cGAS protein was stimulated by DNA but not RNA.

We also expressed m-cGAS in $E.$ $coli$ as a SUMO fusion protein. After purification, Sumo-m-cGAS generated the cGAMP activity in a DNA-dependent manner. However, after the SUMO tag was removed by a Sumo protease, the m-cGAS protein catalyzed cGAMP synthesis in a DNA-independent manner. The reason for this loss of DNA dependency is unclear, but could be due to some conformational changes after Sumo removal. Titration experiments showed that less than 1 nM of the recombinant cGAS protein led to detectable IRF3 dimerization, whereas the catalytically inactive mutant of cGAS failed to activate IRF3 even at high concentrations. To formally prove that cGAS catalyzes the synthesis of cGAMP, the reaction products were analyzed by nano-LC-MS using SRM. cGAMP was detected in a 60-min reaction containing purified cGAS, ATP and GTP. The identity of cGAMP was further confirmed by ion fragmentation using collision-induced dissociation (CID). The fragmentation pattern of cGAMP synthesized by purified cGAS revealed product ions whose m/z values matched those of chemically synthesized cGAMP. Collectively, these results demonstrate that purified cGAS catalyzes the synthesis of cGAMP from ATP and GTP.

cGAS Binds to DNA.

The stimulation of cGAS activity by DNA indicates that c-GAS is a DNA sensor. Indeed, both GST-m-cGAS and GST-h-cGAS, but not GST-RIG-I N-terminus [RIG-I(N)], were precipitated by biotinylated ISD. In contrast, biotinylated RNA did not bind cGAS. Deletion analyses showed that the h-cGAS N-terminal fragment containing residues 1-212, but not the C-terminal fragment 213-522, bound to ISD. A longer C-terminal fragment containing residues 161-522 did bind to ISD, indicating that the sequence 161-212 may be important for DNA binding. However, deletion of residues 161-212 from h-cGAS did not significantly impair ISD binding, indicating that cGAS contains another DNA binding domain at the N-terminus. Indeed, the N-terminal fragment containing residues 1-160 also bound ISD. Thus, cGAS may contain two separate DNA binding domains at the N-terminus. Nevertheless, it is clear that the N-terminus of h-cGAS containing residues 1-212 is both necessary and sufficient to bind DNA.

Different deletion mutants of h-cGAS were overexpressed in HEK293T-STING cells to determine their ability to activate IRF3 and induce IFNβ and the cytokine tumor necrosis factor α (TNFα). The protein fragment 1-382, which lacks the C-terminal 140 residues including much of the Mab21 domain, failed to induce IFNβ or TNFα or to activate IRF3, indicating that an intact Mab21 domain is important for cGAS function. As expected, deletion of the N-terminal 212 residues (fragment 213-522), which include part of the NTase domain, abolished the cGAS activity. An internal deletion of just four amino acids (KLKL, Δ171-174) within the first helix of the NTase fold preceding the catalytic residues also destroyed the cGAS activity. Interestingly, deletion of the N-terminal 160 residues did not affect IRF3 activation or cytokine induction by cGAS. In vitro assay showed that this protein fragment (161-522) still activated the IRF3 pathway in a DNA-dependent manner. Thus, the N-terminal 160 amino acids of h-cGAS, whose primary sequence is not highly conserved evolutionarily, appears to be largely dispensable for DNA binding and catalysis by cGAS. In contrast, the NTase and Mab21 domains are important for cGAS activity.

cGAS is Predominantly Localized in the Cytosol.

To determine if cGAS is a cytosolic DNA sensor, we prepared cytosolic and nuclear extracts from THP1 cells and analyzed the localization of endogenous h-cGAS by immunoblotting. h-cGAS was detected in the cytosolic extracts, but barely detectable in the nuclear extracts. The THP1 extracts were further subjected to differential centrifugation to separate subcellular organelles from one another and from the cytosol. Similar amounts of h-cGAS were detected in S100 and P100 (pellet after 100,000×g centrifugation), indicating that this protein is soluble in the cytoplasm but a significant fraction of the protein is associated with light vesicles or organelles. The cGAS protein was not detected in P5, which contained mitochondria and ER as evidenced by the presence of VDAC and STING, respectively. cGAS was also not detectable in P20, which contained predominantly ER and heavy vesicles.

We also examined the localization of cGAS by confocal immunofluorescence microscopy using L929 cells stably expressing Flag-m-cGAS. The cGAS protein distributed throughout the cytoplasm but could also be observed in the nuclear or peri-nuclear region. Interestingly, after the cells were transfected with Cy3-labelled ISD for 2 or 4 hours, punctate forms of cGAS were observed and they overlapped with the DNA fluorescence. Such co-localization and apparent aggregation of cGAS and Cy3-ISD was observed in more than 50% of the cells under observation. These results, together with the biochemical evidence of direct binding of cGAS with DNA, indicate that cGAS binds to DNA in the cytoplasm.

Discussion.

In this example, we developed a strategy that combined quantitative mass spectrometry with conventional protein purification to identify biologically active proteins that were partially purified from crude cell extracts. This strategy is generally applicable to proteins that are difficult to be purified to homogeneity due to very low abundance, labile activity or scarce starting materials. As a proof of principle, we used this strategy to identify the mouse protein E330016A19 as the enzyme that synthesizes cGAMP. This discovery led to the identification of a large family of cGAS that is conserved from fish to human, formally demonstrating that vertebrate animals contain evolutionarily conserved enzymes that synthesize cyclic di-nucleotides, which were previously found only in bacteria, archaea and protozoan (11-13). $Vibrio$ $cholera$ can synthesize cGAMP through its cyclase DncV (VC0179), which contains an NTase domain, but lacks significant primary sequence homology to the mammalian cGAS (12).

Our results not only demonstrate that cGAS is a cytosolic DNA sensor that triggers the type-I interferon pathway, but also reveal a novel mechanism of immune signaling in which cGAS generates the second messenger cGAMP, which binds to and activates STING (4), thereby triggering type-I interferon production. The deployment of cGAS as a cytosolic DNA sensor greatly expands the repertoire of microorganisms detected by the host immune system. In principle, all microorganisms that can carry DNA into the host cytoplasm, such as DNA viruses, bacteria, parasites (e.g., malaria) and retroviruses (e.g., HIV), could trigger the cGAS-STING pathway (14, 15). The enzymatic synthesis of cGAMP by cGAS provides a mechanism of signal amplification for a robust and sensitive immune response. However, the detection of self DNA in the host cytoplasm by cGAS can also lead to autoimmune diseases, such as systemic lupus erythematosus, Sjögren's syndrome, and Aicardi-Goutières syndrome (16-18).

Several other DNA sensors, such as DAI, IFI16 and DDX41, have been reported to induce type-I interferons (19-21). Overexpression of DAI, IFI16 or DDX41 did not lead to the production of cGAMP. We also found that knockdown of DDX41 and p204 (a mouse homologue of IFI16) by siRNA did not inhibit the generation of cGAMP activity in HT-DNA transfected L929 cells. Unlike other putative DNA sensors and most pattern recognition receptors (e.g., TLRs), cGAS is a cyclase that is amenable to inhibition by small molecule compounds, which provide therapeutic agents for the treatment of human autoimmune diseases.

REFERENCES AND NOTES

1. L. A. O'Neill, DNA makes RNA makes innate immunity. *Cell* 138, 428 (Aug. 7, 2009).
2. G. N. Barber, Cytoplasmic DNA innate immune pathways. *Immunological reviews* 243, 99 (September, 2011).
3. S. E. Keating, M. Baran, A. G. Bowie, Cytosolic DNA sensors regulating type I interferon induction. *Trends in immunology* 32, 574 (December, 2011).
4. J. Wu et al., Cyclic-GMP-AMP is an endogenous second messenger in innate immune signaling by cytosolic DNA. *Science*, (2012).
5. J. Cox, M. Mann, MaxQuant enables high peptide identification rates, individualized p.p.b.-range mass accuracies and proteome-wide protein quantification. *Nat Biotechnol* 26, 1367 (December, 2008).
6. K. Kuchta, L. Knizewski, L. S. Wyrwicz, L. Rychlewski, K. Ginalski, Comprehensive classification of nucleotidyltransferase fold proteins: identification of novel families and their representatives in human. *Nucleic Acids Res* 37, 7701 (December, 2009).
7. K. L. Chow, D. H. Hall, S. W. Emmons, The mab-21 gene of *Caenorhabditis elegans* encodes a novel protein required for choice of alternate cell fates. *Development* 121, 3615 (November, 1995).
8. J. Pei, B. H. Kim, N. V. Grishin, PROMALS3D: a tool for multiple protein sequence and structure alignments. *Nucleic Acids Res* 36, 2295 (April, 2008).
9. J. W. Schoggins et al., A diverse range of gene products are effectors of the type I interferon antiviral response. *Nature* 472, 481 (Apr. 28, 2011).
10. Y. H. Chiu, J. B. Macmillan, Z. J. Chen, RNA polymerase III detects cytosolic DNA and induces type I interferons through the RIG-I pathway. *Cell* 138, 576 (Aug. 7, 2009).
11. C. Pesavento, R. Hengge, Bacterial nucleotide-based second messengers. *Curr Opin Microbiol* 12, 170 (April, 2009).
12. B. W. Davies, R. W. Bogard, T. S. Young, J. J. Mekalanos, Coordinated regulation of accessory genetic elements produces cyclic di-nucleotides for *V. cholerae* virulence. *Cell* 149, 358 (Apr. 13, 2012).
13. Z. H. Chen, P. Schaap, The prokaryote messenger c-di-GMP triggers stalk cell differentiation in Dictyostelium. *Nature* 488, 680 (Aug. 30, 2012).
14. S. Sharma et al., Innate immune recognition of an AT-rich stem-loop DNA motif in the Plasmodium falciparum genome. *Immunity* 35, 194 (Aug. 26, 2011).
15. N. Yan, Z. J. Chen, Intrinsic antiviral immunity. *Nat Immunol* 13, 214 (2012).
16. V. Pascual, L. Farkas, J. Banchereau, Systemic lupus erythematosus: all roads lead to type I interferons. *Current opinion in immunology* 18, 676 (December, 2006).
17. Y. Yao, Z. Liu, B. Jallal, N. Shen, L. Ronnblom, Type I Interferons in Sjogren's Syndrome. *Autoimmunity reviews*, (Nov. 29, 2012).
18. R. E. Rigby, A. Leitch, A. P. Jackson, Nucleic acid-mediated inflammatory diseases. *Bioessays* 30, 833 (September, 2008).
19. A. Takaoka et al., DAI (DLM-1/ZBP1) is a cytosolic DNA sensor and an activator of innate immune response. *Nature* 448, 501 (Jul. 26, 2007).
20. L. Unterholzner et al., IFI16 is an innate immune sensor for intracellular DNA. *Nature immunology* 11, 997 (November, 2010).
21. Z. Zhang et al., The helicase DDX41 senses intracellular DNA mediated by the adaptor STING in dendritic cells. *Nature immunology* 12, 959 (October, 2011).
22. The GenBank accession numbers for human and mouse cGAS sequences are KC294566 and KC294567.

Example 3

Cyclic GMP-AMP Containing Mixed Phosphodiester Linkages is an Endogenous High Affinity Ligand for STING Innate immune sensing of microbial infections is mediated by germline-encoded pattern recognition receptors that include membrane proteins such as Toll-like receptors (TLRs) and cytosolic proteins such as NOD-like receptors (NLRs) and RIG-I like receptors (RLRs)(Iwasaki and Medzhitov, 2010; Ronald and Beutler, 2010; Takeuchi and Akira, 2010). As virtually all infectious microorganisms contain and need nucleic acids in their life cycles, the innate immune system has evolved to recognize the microbial DNA and RNA as a central strategy of host defense. Specifically, several TLRs are localized on the endosomal membrane to detect RNA or DNA in the lumen of the endosomes, whereas RLRs are responsible for detecting viral and bacterial RNA in the cytoplasm.

DNA is known to be an immune stimulatory molecule for more than a century, but how DNA activates the host immune system has not been extensively investigated until recently (O'Neill, 2013). DNA in the endosome is detected by TLR9, which then triggers the production of type-I interferons and inflammatory cytokines. When microbial or host DNA is delivered to the cytoplasm, it can also induce type-I interferons through the endoplasmic reticulum membrane protein STING (also known as MITA, ERIS or MPYS) (Barber, 2011). STING functions as an adaptor protein that recruits and activates the protein kinases IKK and TBK1, which in turn activate the transcription factors NF-κB and IRF3 to induce interferons and other cytokines.

We recently identified cyclic GMP-AMP Synthase (cGAS) as a DNA sensor that activates STING (Sun et al., 2013; Wu et al., 2013). Specifically, we found that cGAS catalyzes the synthesis of cyclic GMP-AMP (cGAMP) from ATP and GTP in the presence of DNA. cGAMP then functions as a second messenger that binds to and activates STING. While these studies clearly demonstrate that cGAMP is an endogenous second messenger produced by cGAS in mammalian cells, the exact nature of the internal phosphodiester linkages between GMP and AMP in cGAMP was not determined in part because mass spectrometry alone could not unambiguously distinguish these linkages without the availability of all cGAMP isomers as the standard reference. Although chemically synthesized cGAMP that contains homogenous 3'-5' linkages is capable of inducing IFNβ, it remained possible that cGAMP containing other phosphodiester linkages might also activate the STING pathway.

In this study, we further investigated the structure of cGAMP through a combination of chemical and biophysical techniques. We found that cGAMP produced by cGAS contains a phosphodiester linkage between 2'-OH of GMP and 5'-phosphate of AMP and another between 3'-OH of AMP and 5'-phosphate of GMP. We further showed that this molecule, herein referred to as 2'3'-cGAMP, was produced in mammalian cells in response to DNA in the cytoplasm. Moreover, we demonstrated that 2'3'-cGAMP binds to STING with a high affinity and is a potent inducer of interferon-β (IFNβ). We also solved the crystal structure of STING bound to the cGAS product and observed extensive interactions between 2'3'-cGAMP and STING, which provide the structural basis for their specific and high affinity binding. Importantly, the structure of the STING-cGAMP complex revealed that this natural ligand induces conformational rearrangements in STING underlying its activation.

The Product of cGAS is Cyclic GMP-AMP Containing Mixed Phosphodiester Bonds.

Both 2'-5' and 3'-5' phosphodiester linkages between nucleotides are known to exist in nature while the 2'-5' linkage is less common. The internal phosphodiester linkages of the natural cGAMP produced by cGAS remain to be determined. We therefore chemically synthesized cGAMP molecules containing all four possible phosphodiester linkages (Table S1). The chemical synthesis of cGAMP isoforms was performed using procedures modified from published methods (Gaffney et al., 2010; Zhang et al., 2006). For simplicity, we name these cGAMP molecules according to the OH position of GMP followed by the OH position of AMP that form the phosphodiester bonds; for example, 2'3'-cGAMP contains a phosphodiester linkage between 2'-OH of GMP and 5'-phosphate of AMP and another between 3'-OH of AMP and 5'-phosphate of GMP. We also used purified cGAS protein to enzymatically synthesize the natural cGAMP from ATP and GTP in the presence of DNA (Sun et al., 2013). The purified cGAS product and synthetic cGAMP isomers were analyzed by nuclear magnetic resonance (NMR) spectroscopy. Strikingly, the $^1$H NMR spectrum of the cGAS product was identical to that of synthetic 2'3'-cGAMP, but distinct from those of other cGAMP isomers. In particular, the anomeric proton (H1') was a singlet with a 3'-phosphate and a doublet with 2'-phosphate. Consistently, only the phosphates of 2',3'-cGAMP had the same $^{31}$P NMR chemical shifts as those of natural cGAMP. We also performed mass spectrometry analysis of the natural and synthetic cGAMP using Q-Exactive, an instrument with high resolution and mass accuracy. The total mass of each of these singly charged molecules ([M+H]$^+$) was 675.107, exactly matching the theoretical mass of cGAMP. The tandem mass (MS/MS) spectra of the cGAS product, which was fragmented using higher energy collision dissociation (HCD), were identical to those of synthetic 2'3'-cGAMP, and similar but not identical to those of 2'2'-cGAMP and 3'3'-cGAMP. The MS/MS spectra of 3'2'-cGAMP appeared to be most distinct from those of 2'3'-cGAMP and the cGAS product. Reverse phase HPLC analysis showed that natural cGAMP co-eluted with 2'3'-cGAMP, but not other cGAMP molecules. We also determined the configuration of the cGAS product by circular dichroism (CD), confirming that it is derived from D-ribose. The CD spectrum of the natural cGAMP overlapped well with that of 2'3'-cGAMP. The near-UV CD spectra indicate that the four cGAMPs adopt significantly different conformations, with 2'3' and 2'2'-cGAMPs forming a CD band pattern distinct from those of 3'2'- and 3'3'-cGAMPs. Collectively, these results provide definitive proof that cGAS synthesizes 2'3'-cGAMP in vitro.

Endogenous cGAMP Produced in DNA-Transfected Cells Contains Mixed Phosphodiester Bonds.

To test whether mammalian cells could produce endogenous cGAMP that contains the mixed phosphodiester linkages, we transfected the mouse cell line L929 and human monocytes THP1 with herring testis DNA (HT-DNA), then cell lysates were heated at 95° C. to denature proteins and the supernatants were prepared for analysis of endogenous cGAMP by mass spectrometry (Wu et al., 2013). The MS/MS spectra of the endogenous molecule from both cell lines were identical to those of cGAS product and 2'3'-cGAMP, indicating that the endogenous second messenger is 2'3'-cGAMP.

2'3'-cGAMP is a High Affinity Ligand of STING.

We performed isothermal titration calorimetry experiments to measure the affinity ($K_d$) of STING binding to natural and synthetic cGAMP. A C-terminal domain (CTD) encompassing residues 139-379 of human STING, which was previously shown to mediate binding to the bacterial second messenger cyclic di-GMP (Burdette et al., 2011; Huang et al., 2012; Ouyang et al., 2012; Shang et al., 2012; Shu et al., 2012; Yin et al., 2012), was expressed in *E. coli* and purified to apparent homogeneity for the ITC experiment. Consistent with previous reports, we found that c-di-GMP bound to STING with a $K_d$ of 1.21 uM. Interestingly, both natural cGAMP and synthetic 2'3'-cGAMP bound to STING with such a high affinity that curve fitting was difficult. In addition, unlike the binding of c-di-GMP, which is an exothermic process, the binding of natural and 2'3'-cGAMP to STING was endothermic, suggesting that the energy may be used for STING conformational change (see below). To obtain the $K_d$ of natural and synthetic 2'3'-cGAMP for STING, we titrated different amounts of these compounds as competitors into the STING-c-di-GMP complex. These measurements yielded a $K_d$ of 4.59 nM for the cGAS product and 3.79 nM for 2'3'-cGAMP. The competition experiment was also performed for 3'2'-cGAMP, because its binding to STING generated little heat change. This compound binds to STING with a $K_d$ of 1.61 uM. 2'2'- and 3'3'-cGAMP were titrated directly to STING and the $K_d$ values were calculated to be 287 nM and 1.04 uM, respectively. Thus, the $K_d$ of 2'3'-cGAMP was ~300 fold lower than those of c-di-GMP, 3'2'-cGAMP and 3'3'-cGAMP, and ~75 fold lower than that of 2'2'-cGAMP.

cGAMPs are Potent Inducers of Type-I Interferons.

We delivered different amounts of the cGAMP isomers as well as c-di-GMP into L929 cells and measured IFNβ induction by q-RT-PCR. The cGAMP molecules induced IFNβ with an $EC_{50}$ that ranged from 15 nM to 42 nM, whereas c-di-GMP had an $EC_{50}$ of greater than 500 nM. Thus, it appeared that the binding affinity of different cyclic di-nucleotides did not correlate well with their $EC_{50}$ in the cell-based assays. The reason for this is not clear, but it is possible that different compounds have different stability or distribution in the cells. Nevertheless, these experiments provide direct evidence that the cGAS product, 2'3'-cGAMP, is a high affinity ligand for STING ($K_d$: ~4 nM) and a potent inducer of IFNβ in cells ($EC_{50}$: ~20 nM).

The Crystal Structure of STING-cGAMP Complex Reveals Ligand-Induced Conformational Rearrangements of STING.

We co-crystallized the STING C-terminal domain (CTD) (residues 139-379) with the purified cGAS product in the C2 space group. The structure of the complex was solved by molecular replacement using an apo-STING structure (PDB code: 4F9E) as the search model and was refined to 1.88 Å resolution (Table M1). There is one STING protomer in the crystallographic asymmetric unit, which forms a butterfly-shaped dimer with another protomer that is related by the crystallographic two-fold symmetry. The bound cGAMP molecule sits at the two-fold axis (see details below). The ordered region of STING (from Asn152 to Glu336) adopts an overall structure similar to the apo-STING, characterized by a central twisted β sheet surrounded by four α helices. However, STING in complex with cGAMP displays several striking differences from apo-STING in both the structure of the monomer and the arrangement of the dimer. Compared with the apo-dimer, the two protomers in the dimer of the complex structure undergo substantial inward rotations in relation to the cGAMP binding site. This more closed arrangement creates a deeper pocket between the two protomers to embrace cGAMP. In addition, the cGAMP binding site is covered by a lid of four-stranded anti-parallel n-sheet and the connecting loops formed by residues 219-249 from each of the two protomers. In contrast, this segment in the apo-structure is largely disordered (Ouyang et al., 2012; Yin et al., 2012). The formation of the β sheet is not due to crystallographic packing. The interdomain interactions within the lid involve several pairs of polar contacts, between the side group of Tyr245 and the main-chain carbonyl oxygen atom of Gly234, the side group of Ser243 and the main-chain amide nitrogen atom of Lys236, as well as the side groups of Asp237 and Lys224.

Extensive Interactions Between 2'3'-cGAMP and STING Underlie Their Specific and High Affinity Binding.

Since the crystallographic two-fold axis passes through the asymmetric 2'3'-cGAMP molecule, cGAMP must adopt two orientations related by the two-fold symmetry. This is consistent with the fact that the two protomers in the STING dimer are expected to have equal probabilities to interact with either the guanidine or the adenosine moiety. We therefore assigned two alternative conformations with the occupancy of 0.5 for cGAMP and several surrounding amino acid residues. Simulated annealing omit map of the refined structure shows decent density for cGAMP. 2'3'-cGAMP, but not other isoforms, fits the electron density map well. Compared to c-di-GMP bound to STING, cGAMP sits ~2.5 Å deeper in the crevice between the STING dimeric interface. In addition, the two wings of the butterfly are ~20 Å closer to each other in the STING:cGAMP structure due to the more closed arrangement of the two STING protomers. Further analyses of the cGAMP binding pocket show that cGAMP is well coordinated by extensive polar and hydrophobic interactions. The rings of cGAMP purine base groups stack against four around aromatic residues, Tyr 240 and Tyr167 from each of the two protomers. Notably, the two α-phosphate groups of cGAMP contact Arg238 from both of the two protomers and Arg232 from one protomer. The free 3'-OH of GMP points to two Ser162 residues from the lower part of the pocket. The guanine base directly interacts with the side groups of Glu260 and Thr263, as well as the main-chain carbonyl oxygen of Val239. These unique polar contacts explain why 2'3'-cGAMP is a specific and high affinity ligand for STING. Besides, residues from the β-sheet (Arg232, Arg238, Val239), which are involved in the cGAMP binding, are likely to control the formation of the lid and further activation of STING.

Arginine 232 of STING is Important for the Cytosolic DNA Signaling Pathway.

Three previous reports of the crystal structures of STING bound to cyclic-di-GMP used a rare human variant that substitutes Arg232 with a histidine (Ouyang et al., 2012; Shu et al., 2012; Yin et al., 2012). Extensive sequencing of DNA from human populations has shown that the Arg232 allele is prevalent and thus should be considered wild-type STING (Jin et al., 2011). The use of the H232 variant of STING may explain why c-di-GMP did not induce a significant conformational change of STING in these studies (Ouyang et al., 2012; Shu et al., 2012; Yin et al., 2012). A previous report showed that a mutation of Arg231 of mouse STING (equivalent to Arg232 in human STING) to alanine abolished IFNβ induction by cyclic-di-GMP, but not DNA (Burdette et al., 2011). However, based on our crystal structure of the STING-cGAMP complex, a mutation of Arg232 to histidine is expected to significantly weaken cGAMP binding and downstream signaling by STING, and a mutation of Arg232 to alanine should be even more detrimental. We therefore investigated the function of Arg232 of STING in two sets of experiments. First, we knocked down endogenous STING by RNAi in L929 cells and replaced it with WT, R232A or R232H of human STING. These stable cell lines were transfected with HT-DNA or treated with 2'3'-cGAMP, followed by measurement of IFNβ by q-RT-PCR. The cells expressing WT STING were able to induce IFNβ in response to DNA or cGAMP stimulation, whereas those expressing either R232A or R232H were defective. As a control, the double stranded RNA analogue poly[I:C] stimulated IFNβ expression in all of these cell lines. Second, we stably expressed WT or mutant STING in HEK293T cells, which have undetectable expression of endogenous STING and cGAS (Sun et al., 2013). The cells were then transfected with the human cGAS expression plasmid followed by measurement of IFNβ RNA. WT STING, but not the R232A mutant, was able to support IFNβ induction by cGAS. The R232H mutant was partially defective, possibly because the positively charged histidine may weakly substitute for some of the functions of Arg232. MAVS, an essential adaptor protein of the RIG-I pathway (Seth et al., 2005), was able to induce IFNβ in all of these cell lines. Taken together, our structural and functional data strongly indicate an important role of Arg232 in the functions of STING and further underscore the role of cGAS as an indispensable cytosolic DNA sensor.

Discussion.

Our previous studies identified cGAS as a cytosolic DNA sensor and a cyclase that synthesizes cGAMP using ATP and GTP as the substrates (Sun et al., 2013; Wu et al., 2013). cGAMP then functions as a second messenger that binds to and activates STING. Here we employed chemical synthesis and several biophysical approaches to further characterize the internal phosphodiester linkages of the cGAS product and determined that it is 2'3'-cGAMP. Subsequently, Gao et al reported the structures of cGAS in its apo- and DNA-bound forms, which confirmed that cGAS is indeed a DNA-activated cyclic-GMP-AMP synthase that catalyzes the synthesis of cGAMP from ATP and GTP (Gao et al., 2013). This elegant study also elucidated the structural mechanism by which DNA binding leads to the activation of cGAS. Using a different approach, Gao et al also found that the truncated cGAS protein synthesizes 2'3'-cGAMP in vitro. However, they did not test whether 2'3'-cGAMP has any biological or biochemical activity, nor did they show whether endogenous 2'3-cGAMP is produced in mammalian cells. In this report, we show that stimulation of mouse and human cells with DNA leads to the production of endogenous 2'3'-cGAMP. Moreover, we demonstrate that 2'3'-cGAMP binds to STING with a much greater affinity than other cGAMP isomers and c-di-GMP. We further show that 2'3'-cGAMP and other cGAMP isomers are much more potent than c-di-GMP in inducing IFNβ in cells.

Further insights into the structure and function of 2'3'-cGAMP are gained from the crystal structure of the STING CTD bound to this endogenous ligand. This crystal structure has a resolution of 1.88 Å, allowing for a detailed view of the ligand structure, including both 2'-5' and 3'-5'phosphodiester linkages. The structure reveals specific residues on STING that mediate the binding of 2'3'-cGAMP. Furthermore, a comparison of this structure to the previously published STING CTD structures in its apo form reveals extensive conformational rearrangements induced by the natural ligand. Specifically, the two arms of the V shaped STING dimer move closer by about 20 Å and a new four n-stranded sheet forms a lid above the cGAMP binding site in the ligand-bound STING structure. These features are absent in the previously determined STING:c-di-GMP structures, which used a STING variant containing the R232H mutation. In these structures, c-di-GMP binding does not induce any obvious conformational rearrangement in STING (Ouyang et al., 2012; Shu et al., 2012; Yin et al., 2012). However, in two other structures containing the WT STING (Arg232) and c-di-GMP, one exhibits similar conformational changes as observed in the STING-cGAMP complex (Huang et al., 2012), and the other shows a distinct conformational change in that Arg232 is oriented differently (Shang et al., 2012). The "closed" conformation observed by Huang et al may have captured the active state of STING induced by c-di-GMP, which is capable of activating STING, albeit more weakly than cGAMP.

The extensive interactions between STING and 2'3'-cGAMP provide the structural basis for their high affinity binding. In particular, Glu260, Thr263 and Val239 interact with the guanine base of GMP and Ser162 interacts with the free 3'-OH group of GMP, explaining why cGAMP containing a phosphodiester bond between 2'-OH of GMP and 5'-phosphate of AMP is a high affinity ligand. In addition, the two α-phosphate groups interact with Arg232 from one protomer and Arg238 from both protomers. This structural analysis explains that the R232A or R232H mutations strongly impair the function of STING in response to DNA or cGAMP. Our data highlight the importance of using the wild-type (Arg232) STING in structural and functional studies.

Although 2'3-cGAMP binds to STING with a much higher affinity than cGAMP isomers containing other phosphodiester linkages, all four cGAMP isomers induced IFNβ with similar $EC_{50}$ values, which were much lower than that of c-di-GMP. Thus, all cGAMP isoforms are potent inducers of IFNβ.

In summary, our results demonstrate that 1) the endogenous second messenger produced in mammalian cells in response to cytosolic DNA stimulation is 2'3'-cGAMP; 2) 2'3'-cGAMP is a high affinity ligand for STING; 3) 2'3'-cGAMP is a potent inducer of IFNβ in mammalian cells; 4) 2'3'-cGAMP induces conformational rearrangements in STING that might underlie its activation; and 5) extensive interactions between 2'3'-cGAMP and STING observed in the crystal structure of the complex explains their specific and high affinity binding.

We conclude: 2'3'-cGAMP is an endogenous second messenger produced by mammalian cells; 2'3'-cGAMP is a high affinity ligand for STING; 2'3'-cGAMP is a potent inducer of type-I interferons; and 2'3'-cGAMP binding induces conformational changes of STING.

Accession Number.

The coordinates of 2'3'-cGAMP bound human STING CTD structure have been deposited in the RCSB protein data bank (PDB: 4KSY).

REFERENCES

GUSSI. on World Wide Web http://biophysicsswmededu/MBR/softwarehtml.

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta crystallographica 66, 213-221.

Barber, G. N. (2011). Cytoplasmic DNA innate immune pathways. Immunological reviews 243, 99-108.

Burdette, D. L., Monroe, K. M., Sotelo-Troha, K., Iwig, J. S., Eckert, B., Hyodo, M., Hayakawa, Y., and Vance, R. E. (2011). STING is a direct innate immune sensor of cyclic di-GMP. Nature 478, 515-518.

DeLano, W. L. (2002). The PyMOL Molecular Graphics System. on World Wide Web http://wwwpymolorg.

Emsley, P., Lohkamp, B., Scott, W. G., and Cowtan, K. (2010). Features and development of Coot. Acta crystallographica 66, 486-501.

Gaffney, B. L., Veliath, E., Zhao, J., and Jones, R. A. (2010). One-flask syntheses of c-di-GMP and the [Rp,Rp] and [Rp,Sp] thiophosphate analogues. Org Lett 12, 3269-3271.

Gao, P., Ascano, M., Wu, Y., Barchet, W., Gaffney, B. L., Zillinger, T., Serganov, A. A., Liu, Y., Jones, R. A., Hartmann, G., et al. (2013). Cyclic [G(2',5')pA(3',5')p] Is the Metazoan Second Messenger Produced by DNA-Activated Cyclic GMP-AMP Synthase. Cell.

Houtman, J. C., Brown, P. H., Bowden, B., Yamaguchi, H., Appella, E., Samelson, L. E., and Schuck, P. (2007). Studying multisite binary and ternary protein interactions by global analysis of isothermal titration calorimetry data in SEDPHAT: application to adaptor protein complexes in cell signaling. Protein Sci 16, 30-42.

Huang, Y. H., Liu, X. Y., Du, X. X., Jiang, Z. F., and Su, X. D. (2012). The structural basis for the sensing and binding of cyclic di-GMP by STING. Nature structural & molecular biology 19, 728-730.

Iwasaki, A., and Medzhitov, R. (2010). Regulation of adaptive immunity by the innate immune system. Science 327, 291-295.

Jin, L., Xu, L. G., Yang, I. V., Davidson, E. J., Schwartz, D. A., Wurfel, M. M., and Cambier, J. C. (2011). Identification and characterization of a loss-of-function human MPYS variant. Genes and immunity 12, 263-269.

Keller, S., Vargas, C., Zhao, H., Piszczek, G., Brautigam, C. A., and Schuck, P. (2012). High-precision isothermal titration calorimetry with automated peak-shape analysis. Analytical chemistry 84, 5066-5073.

Minor, W., Cymborowski, M., Otwinowski, Z., and Chruszcz, M. (2006). HKL-3000: the integration of data reduction and structure solution—from diffraction images to an initial model in minutes. Acta crystallographica 62, 859-866.

O'Neill, L. A. (2013). Immunology. Sensing the dark side of DNA. Science 339, 763-64.

Ouyang, S., Song, X., Wang, Y., Ru, H., Shaw, N., Jiang, Y., Niu, F., Zhu, Y., Qiu, W., Parvatiyar, K. (2012). Structural analysis of the STING adaptor protein reveals a hydrophobic dimer interface and mode of cyclic di-GMP binding. Immunity 36, 1073-86.

Ronald, P. C., and Beutler, B. (2010). Plant and animal sensors of conserved microbial signatures. Science 330, 1061-1064.

Seth, R. B., Sun, L., Ea, C. K., and Chen, Z. J. (2005). Identification and characterization of MAVS, a mitochondrial antiviral signaling protein that activates NF-kappaB and IRF 3. Cell 122, 669-682.

Shang, G., Zhu, D., Li, N., Zhang, J., Zhu, C., Lu, D., Liu, C., Yu, Q., Zhao, Y., Xu, S., et al. (2012). Crystal structures of STING protein reveal basis for recognition of cyclic di-GMP. Nature structural & molecular biology 19, 725-727.

Shu, C., Yi, G., Watts, T., Kao, C. C., and Li, P. (2012). Structure of STING bound to cyclic di-GMP reveals the mechanism of cyclic dinucleotide recognition by the immune system. Nature structural & molecular biology 19, 722-724.

Sun, L., Wu, J., Du, F., Chen, X., and Chen, Z. J. (2013). Cyclic GMP-AMP synthase is a cytosolic DNA sensor that activates the type I interferon pathway. Science 339, 786-791.

Takeuchi, O., and Akira, S. (2010). Pattern recognition receptors and inflammation. Cell 140, 805-820.

Wu, J., Sun, L., Chen, X., Du, F., Shi, H., Chen, C., and Chen, Z. J. (2013). Cyclic GMP-AMP is an endogenous second messenger in innate immune signaling by cytosolic DNA. Science 339, 826-830.

Yin, Q., Tian, Y., Kabaleeswaran, V., Jiang, X., Tu, D., Eck, M. J., Chen, Z. J., and Wu, H. (2012). Cyclic di-GMP sensing via the innate immune signaling protein STING. Molecular cell 46, 735-745.

Zhang, Z., Kim, S., Gaffney, B. L., and Jones, R. A. (2006). Polymorphism of the signaling molecule c-di-GMP. J Am Chem Soc 128, 7015-7024.

TABLE M1

Statistics of data collection and refinement of cGAMP bound STING

| Data | cGAMP bound STING |
|---|---|
| Space Group | C2 |
| Unit Cell (Å, °) | 89.525 77.927 35.974 90 96.98 90 |
| Number of molecules in ASU | 1 |
| Wavelength (Å) | 0.97918 |
| Resolution (Å) | 50-1.88 (1.91-1.88) |
| $R_{merge}$ (%) | 7.8 (65.0) |
| I/σ | 17.82 (2.20) |
| Completeness (%) | 99.4 (98.6) |
| Number of measured reflections | 99,635 |
| Number of unique reflections | 19,800 |
| Redundancy | 5.0 (4.8) |
| Wilson B factor (Å$^2$) | 30.80 |
| R-factor (%) | 16.07 (23.09) |
| $R_{free}$ (%) | 18.15 (30.83) |
| Number of atoms | |
| Macromolecules | 1483 |
| Ligand | 45 |
| Water | 72 |
| All atoms | 1600 |
| Average B value (Å$^2$) | |
| Macromolecules | 46.20 |
| Ligand | 23.10 |
| solvent | 50.00 |
| All atoms | 45.70 |
| Rms deviations from ideal values | |
| Bonds(Å) | 0.007 |
| Angle (°) | 1.213 |
| Ramachandran plot statistics (%) | |
| Favored | 97.22 |
| Allowed | 2.78 |
| Outliers | 0 |

Values in parentheses are for the highest resolution shell. $R = \Sigma |F_{obs} - F_{calc}| / \Sigma F_{obs}$, where Fcalc is the calculated protein structure factor from the atomic model (Rfree was calculated with 10% of the reflections selected).

TABLE S1

Chemical synthesis of cGAMPS.

(A) Synthesis of building blocks S1-S4.

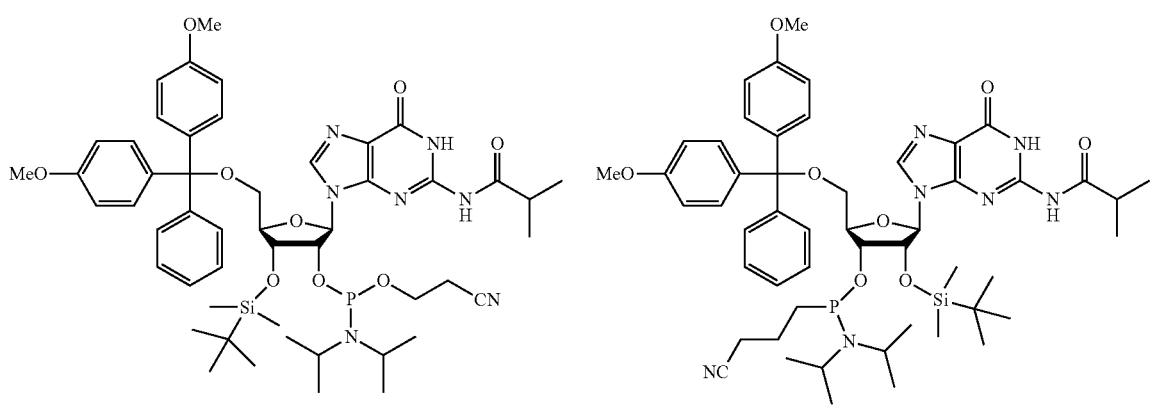

TABLE S1-continued
Chemical synthesis of cGAMPS.
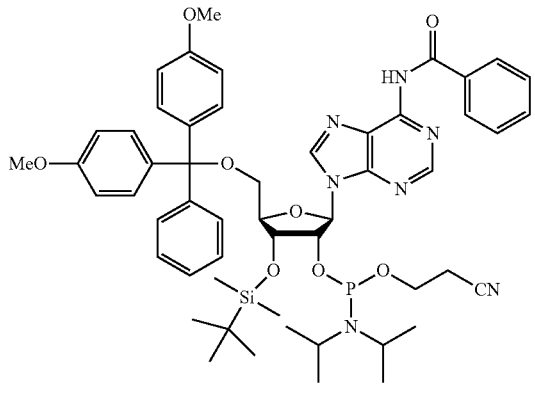
S3
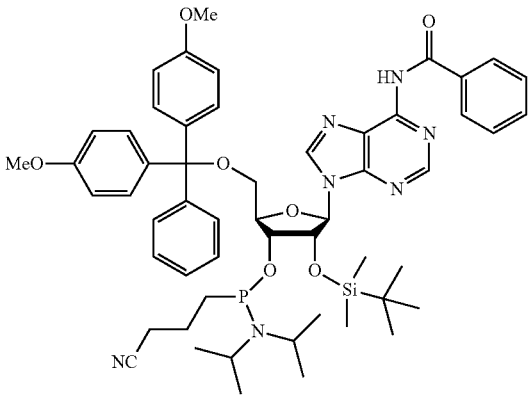
S4
(B) Synthesis of building blocks S1 and S2.
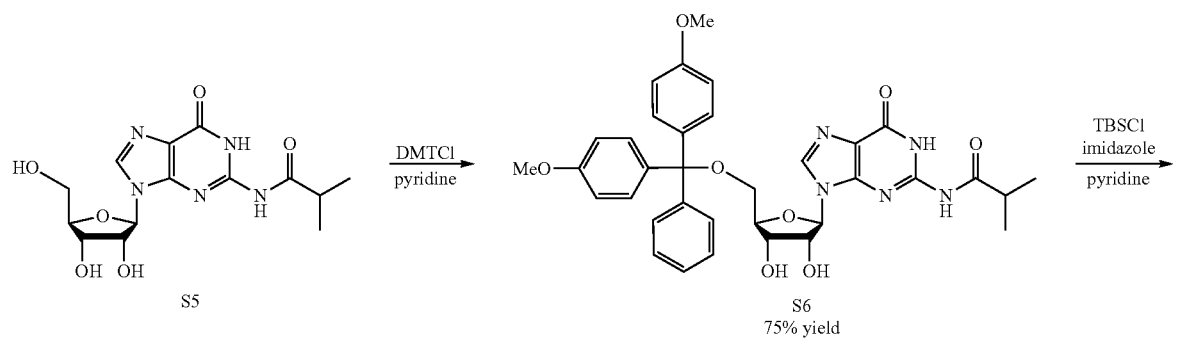
S5 → S6
75% yield
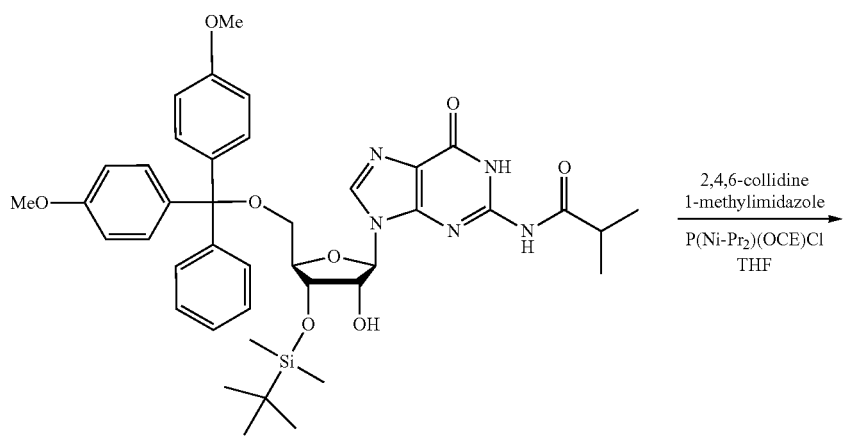
S7
37% yield TABLE S1-continued
Chemical synthesis of cGAMPS.
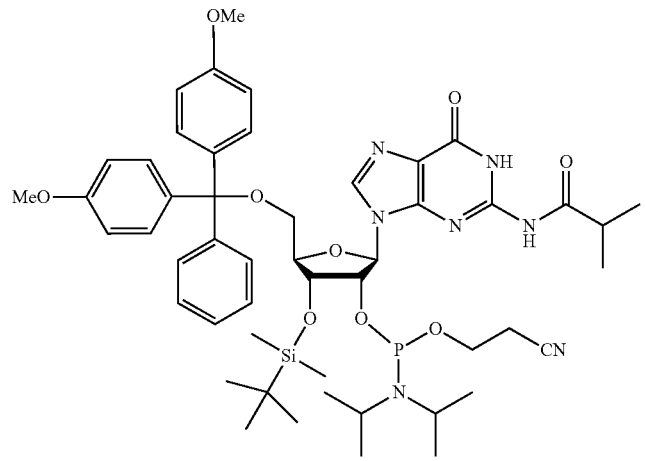
S1
60% yield
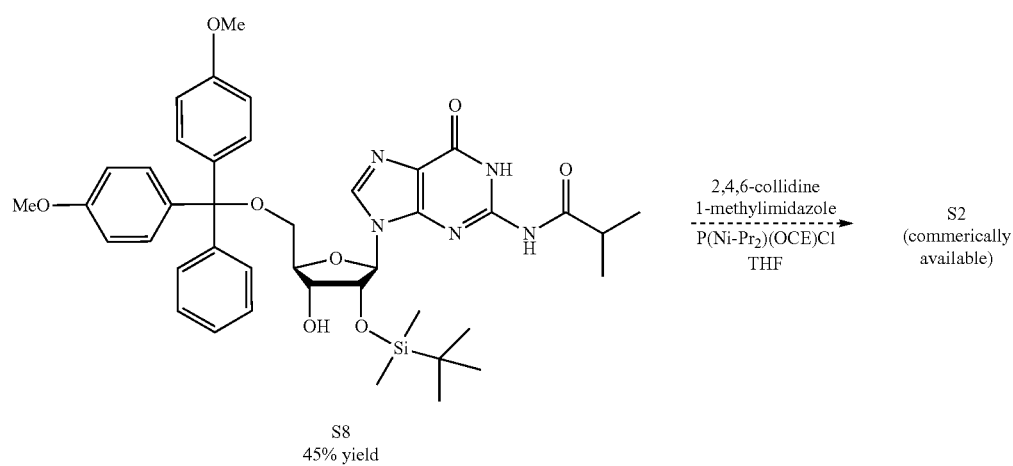
(C) Synthesis of building blocks S3 and S4.
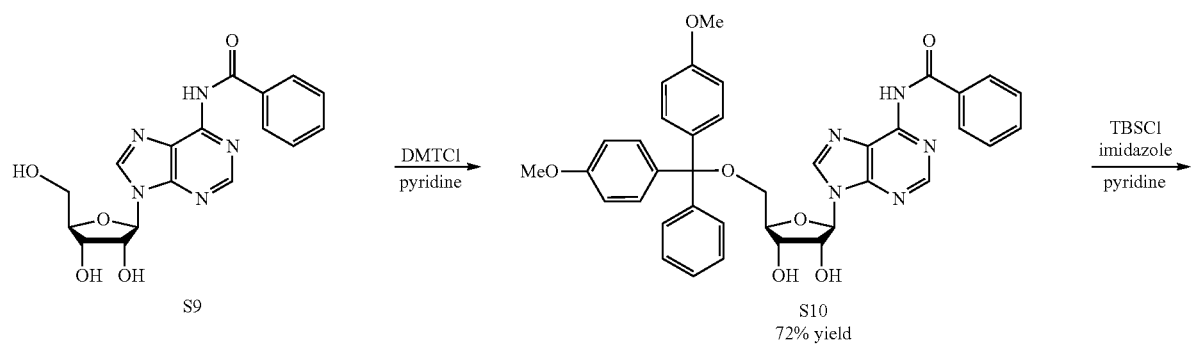

TABLE S1-continued
Chemical synthesis of cGAMPS.
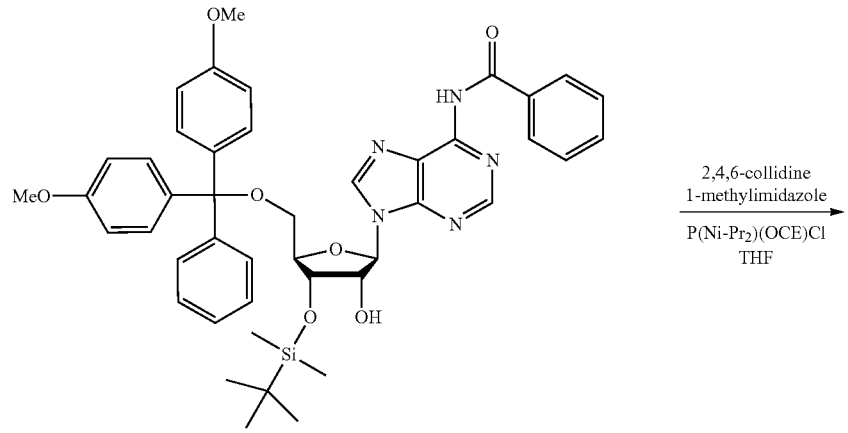
S11
30% yield
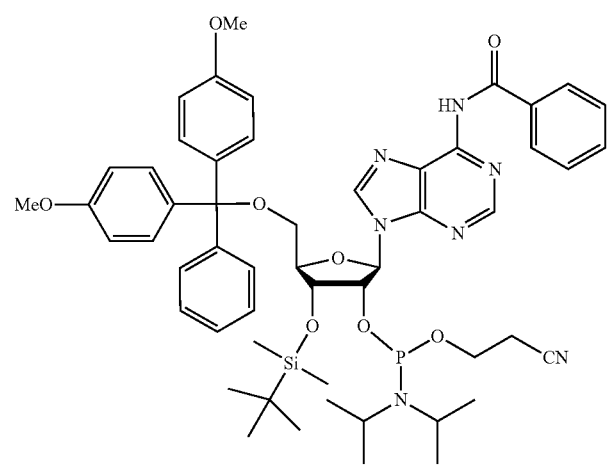
S3
75% yield
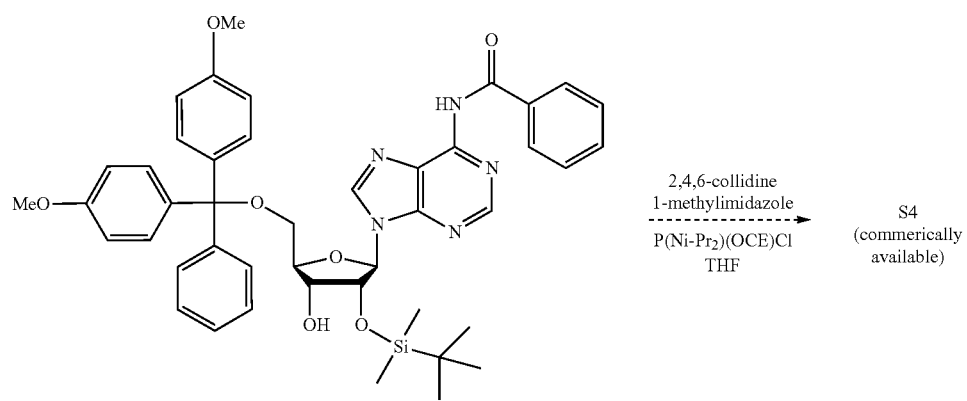
S12
45% yield
S4
(commerically available)

TABLE S1-continued
Chemical synthesis of cGAMPS.
(D) Synthesis of 2'3'-cGAMP.
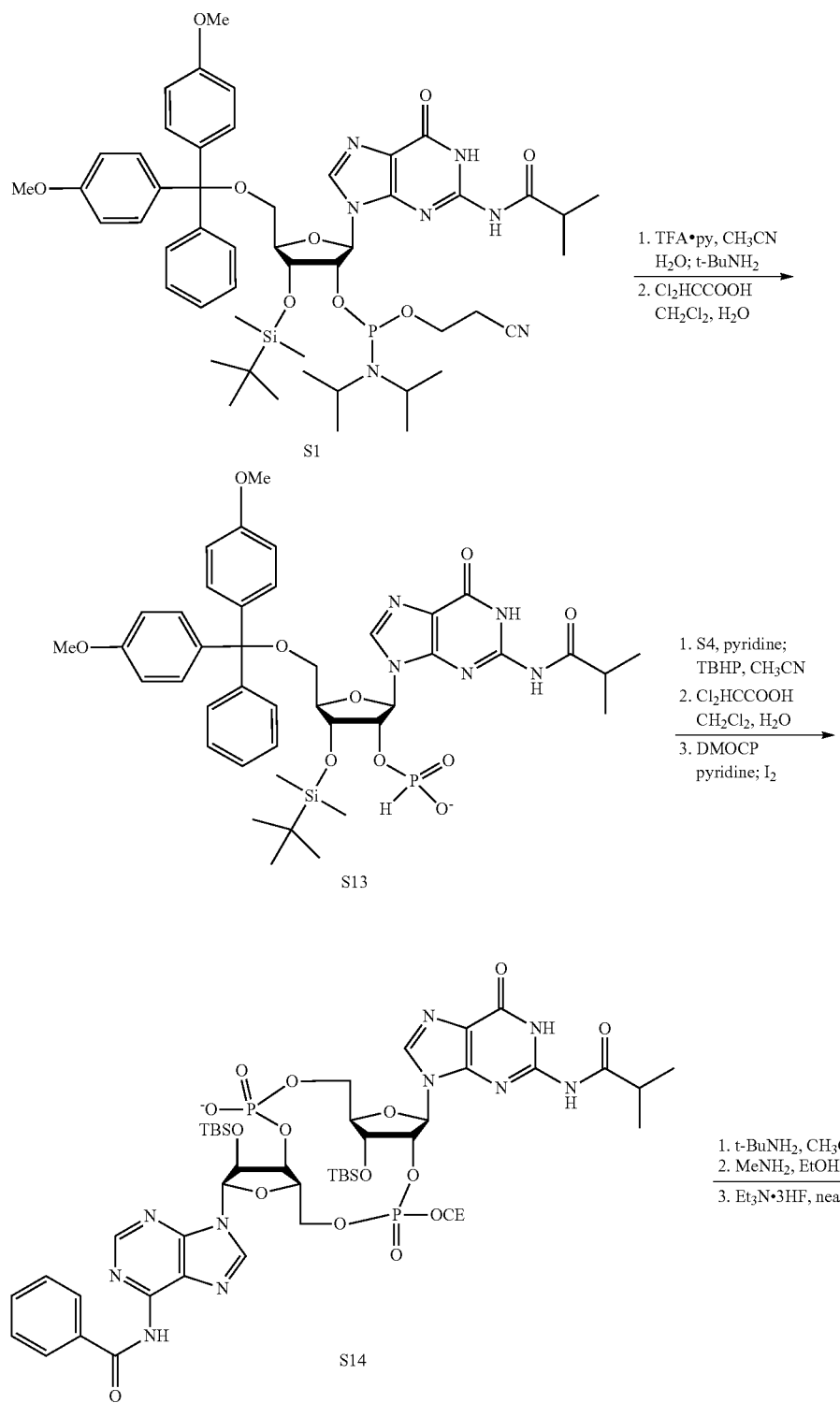

TABLE S1-continued
Chemical synthesis of cGAMPS.
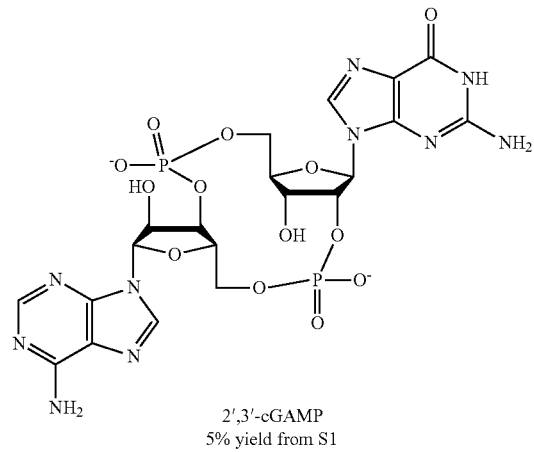
2',3'-cGAMP
5% yield from S1
(E) Synthesis of 2'2'-cGAMP.
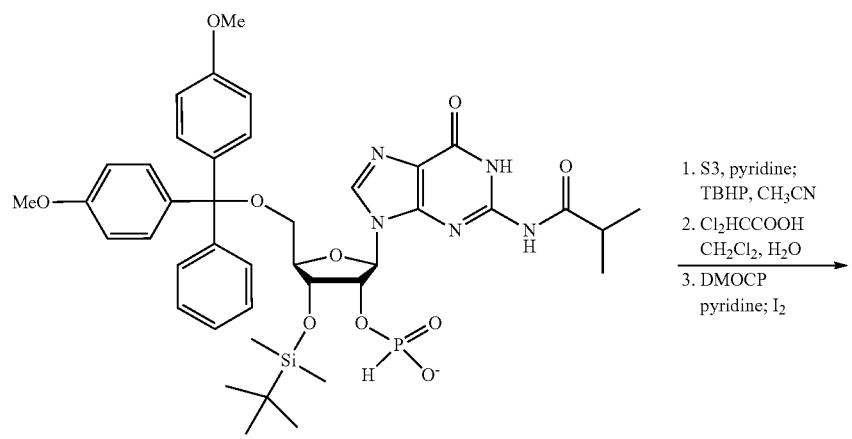
S13
1. S3, pyridine;
   TBHP, CH₃CN
2. Cl₂HCCOOH
   CH₂Cl₂, H₂O
3. DMOCP
   pyridine; I₂
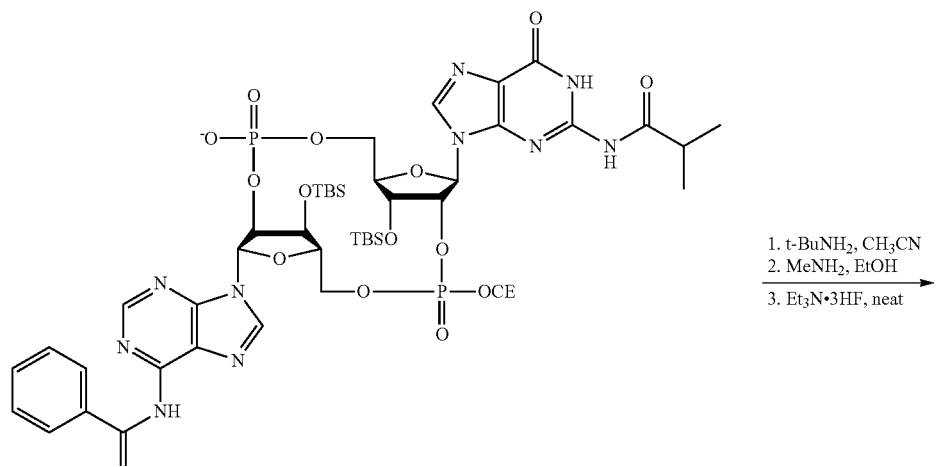
S15
1. t-BuNH₂, CH₃CN
2. MeNH₂, EtOH
3. Et₃N·3HF, neat TABLE S1-continued
Chemical synthesis of cGAMPS.
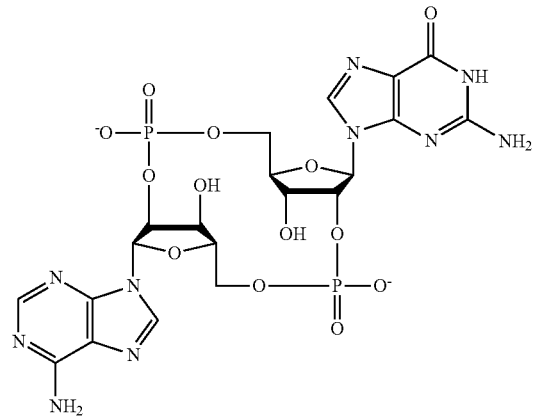
2',2'-cGAMP
5% yield from S1
(F) Synthesis of 3'2'-cGAMP.
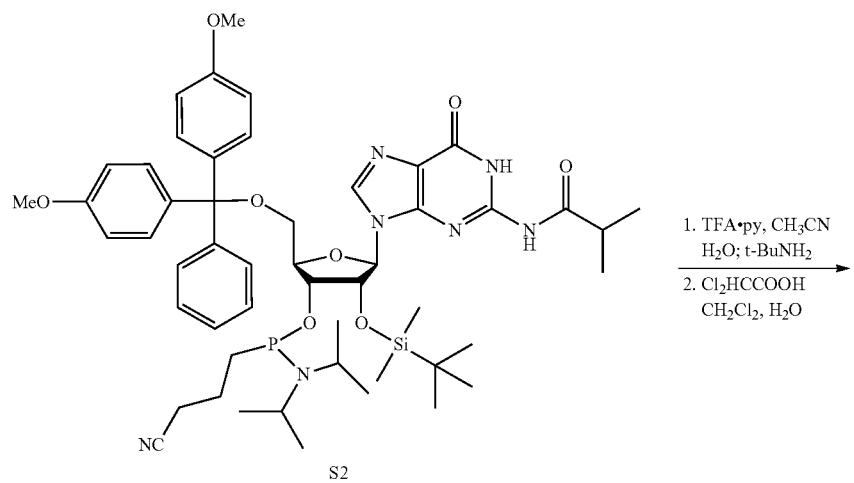
1. TFA·py, CH$_3$CN
   H$_2$O; t-BuNH$_2$
2. Cl$_2$HCCOOH
   CH$_2$Cl$_2$, H$_2$O
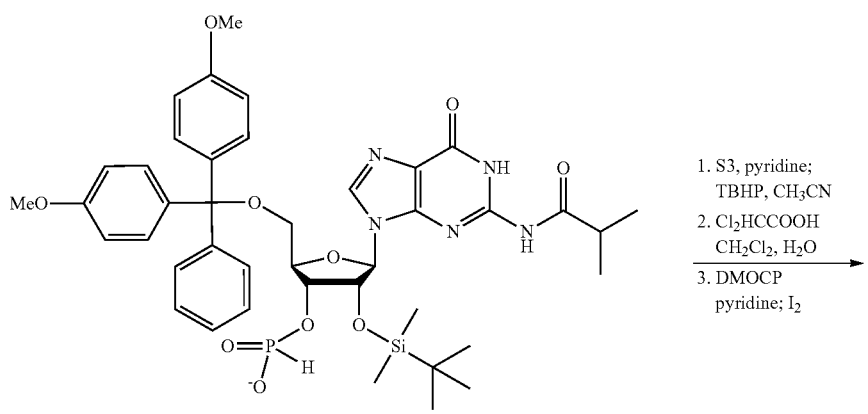
1. S3, pyridine;
   TBHP, CH$_3$CN
2. Cl$_2$HCCOOH
   CH$_2$Cl$_2$, H$_2$O
3. DMOCP
   pyridine; I$_2$ TABLE S1-continued
Chemical synthesis of cGAMPS.
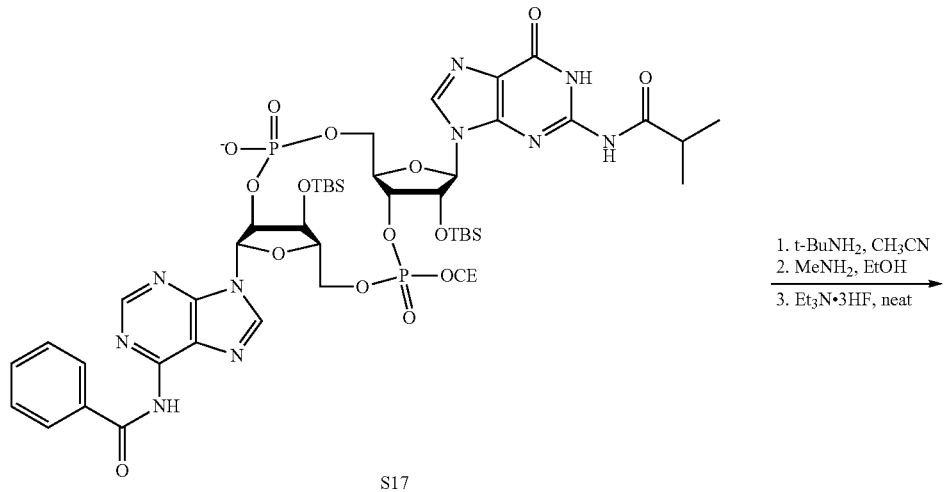
S17
1. t-BuNH$_2$, CH$_3$CN
2. MeNH$_2$, EtOH
3. Et$_3$N•3HF, neat
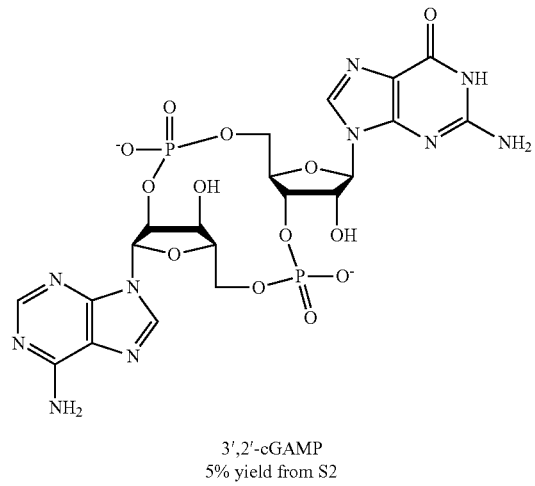
3',2'-cGAMP
5% yield from S2
(G) Synthesis of 3'3'-cGAMP.
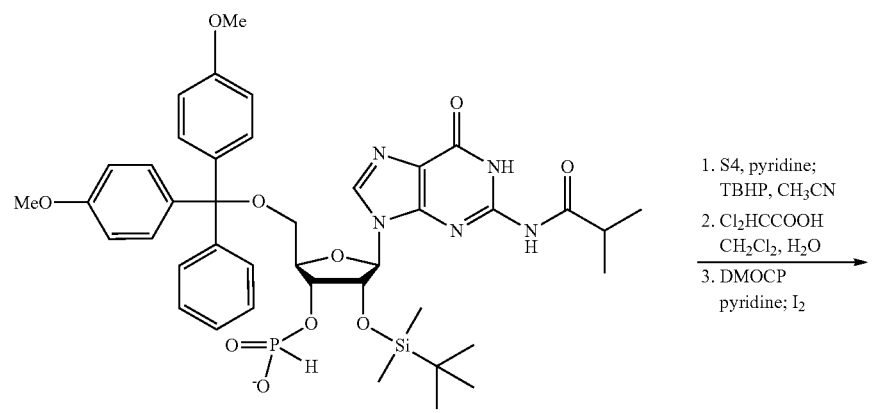
S16
1. S4, pyridine; TBHP, CH$_3$CN
2. Cl$_2$HCCOOH CH$_2$Cl$_2$, H$_2$O
3. DMOCP pyridine; I$_2$ TABLE S1-continued Chemical synthesis of cGAMPS.

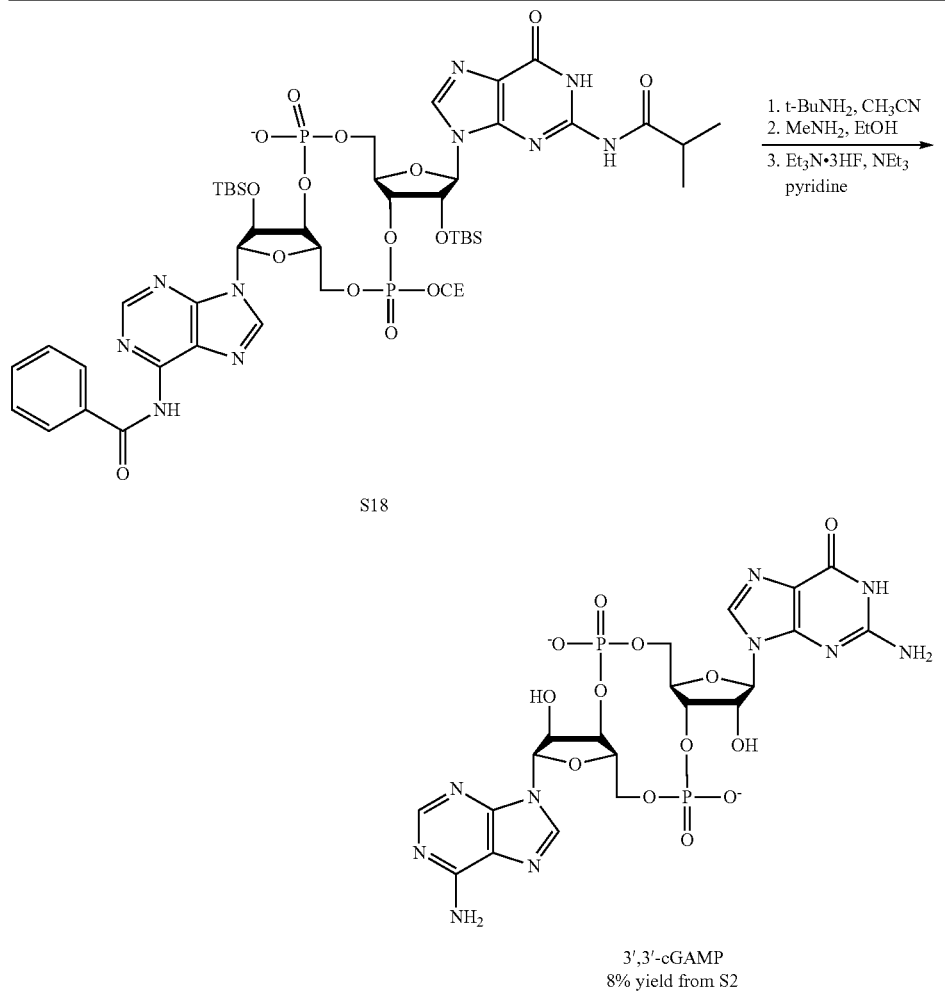

Example 4

Cyclic GMP-AMP Synthase is an Innate Immune Sensor of HIV and Other Retroviruses Retroviruses, including HIV, can activate innate immune responses, but the host sensors for retroviruses are largely unknown. Here we show that HIV infection activates cyclic-GMP-AMP (cGAMP) synthase (cGAS) to produce cGAMP, which binds to and activates the adaptor protein STING to induce type-I interferons and other cytokines. Inhibitors of HIV reverse transcriptase, but not integrase, abrogated interferon-β induction by the virus, indicating that the reverse transcribed HIV DNA triggers the innate immune response. Knockout or knockdown of cGAS in mouse or human cell lines blocked cytokine induction by HIV, murine leukemia virus (MLV) and Simian immunodeficiency virus (SW). These results indicate that cGAS detects retroviral DNA and that cGAS is an innate immune sensor of HW and other retroviruses.

Although tremendous advances have been made in our understanding of innate immune recognition of many microbial pathogens (1-3), relatively little is known about innate immune responses against retroviral infections (4). Retroviruses were thought to trigger weak or no innate immune responses, which were typically measured through the production of inflammatory cytokines and type-I interferons. However, recent research has shown that retroviruses such as HW can trigger innate immune responses, which are normally masked by viral or host factors (5-8). For example, TREX1 is a cytosolic exonuclease that degrades DNA derived from HW or endogenous retroelements, thereby preventing the accumulation of cytosolic DNA which would otherwise trigger innate immunity (9, 10). Loss of function mutations of TREX1 in humans have been closely linked to Aicardi Goutieres Syndrome (AGS), a lupus-like disease characterized by elevated expression of inflammatory cytokines and interferon-stimulated genes (11).

We have recently identified the enzyme cyclic GMP-AMP (cGAMP) synthase (cGAS) as a cytosolic DNA sensor that triggers the production of type-I interferons and other cytokines (12, 13). DNA binds and activates cGAS, which catalyzes the synthesis of a unique cGAMP isomer from ATP and GTP. This cGAMP isomer, termed 2'3'-cGAMP, which contains both 2'-5' and 3'-5' phosphodiester linkages, functions as a second messenger that binds and activates the endoplasmic reticulum protein STING (14-17). STING then activates the protein kinases IKK and TBK1, which in turn activate the transcription factors NF-κB and IRF3 to induce interferons and other cytokines (18). Knockdown of cGAS inhibits IFNβ induction by DNA viruses such as herpes simplex virus-1 (HSV-1) and vaccinia virus (13). Because retroviruses generate complementary DNA from the viral RNA by reverse transcription, we hypothesized that cGAS might detect retroviral DNA and trigger innate immune responses.

We used a single-round HIV-1 virus in which its envelope protein was replaced with the glycoprotein of vesicular stomatitis virus (VSV-G), which allows it to infect a large variety of human and mouse cell types (9). This virus also expresses GFP, which can be used to monitor viral infection. Infection of the human monocytic cell line THP1 with HIV-GFP led to dimerization of IRF3, a hallmark of its activation. Phosphorylation of STAT1 at Tyr-701 was also detected after HIV infection, indicating that the interferon signaling pathway was activated in the virus infected cells (19). HIV infection led to the induction of IFNβ and the chemokine CXCL10, concomitant with the generation of the HIV Gag episomal DNA. The levels of IFNβ production were proportional to the multiplicity of infection by HIV. Treatment of HIV-GFP virus with DNase I did not impair its ability to induce IFNβ, whereas treatment of herring testis DNA (HT-DNA) with DNase I inhibited IFNβ induction, indicating that IFNβ induction by HIV-GFP was not due to any contaminating DNA. Differentiation of THP1 from monocytes to macrophages by treating the cells with phorbol-12-myristate-13-acetate (PMA) inhibited HIV-GFP infection or replication and strongly inhibited IFNβ induction. Thus, unless otherwise indicated, THP1 cells used in our study were not treated with PMA prior to HIV infection.

To test if reverse transcription is required for HIV to activate the innate immune response, we treated THP1 cells with the HIV reverse transcriptase inhibitors, azidothymidine (AZT) and nevirapine (NVP). Both inhibitors blocked IRF3 activation and IFNβ induction by HIV. In contrast, the HIV integrase inhibitor raltegravir (RAL) did not affect the activation of this pathway. AZT and NVP, even at high concentrations, did not inhibit IFNβ induction by HT-DNA, indicating that the inhibitory effects of AZT and NVP were due to their specific inhibition of HIV reverse transcription. These results indicate that the reverse transcribed HIV DNA is the trigger of IRF3 activation and IFNβ production.

Strikingly, shRNA-mediated knockdown of cGAS or STING in THP1 cells strongly inhibited the induction of IFNβ and CXCL10 and the activation of IRF3 by HIV-GFP. Control experiments showed that shRNA against luciferase did not inhibit the activation of the pathway, and that the shRNA vectors knocked down the intended targets specifically. In particular, the cGAS shRNA knocked down cGAS but not STING, and the induction of IFNβ in these cells was rescued by delivering cGAMP into the cells indicating that the cGAS shRNA did not have off-target effects in the STING pathway.

Previous studies have shown that VSV-G pseudotyped HIV-1 strongly induces IFNβ in TREX1-deficient mouse embryonic fibroblasts (MEF) but not in the wild-type (WT) MEF (9). We generated Trex1$^{-/-}$ MEF cell lines stably expressing shRNA against cGAS, STING or luciferase (as a control). HIV infection induced IFNβ and CXCL10 RNA in the control cells (sh-luciferase) but not in cGAS or STING depleted cells. In contrast, knockdown of cGAS or STING did not affect the induction of IFNβ or CXCL10 by the double-stranded RNA analogue poly[I:C].

To obtain definitive evidence for the role of cGAS in the innate sensing of cytosolic DNA and retroviruses, we employed the TALEN technology to disrupt the gene that encodes cGAS (Mb21d1), specifically the region that encodes the catalytic domain, in L929 cells (20). Although L929 cells contain three copies of chromosome 9 that harbors the cGAS gene, DNA sequencing of the TALEN expressing cells identified multiple clones that had deletions in all three chromosomes; three of these clones were chosen for further studies. All three clones contained deletions in the cGAS locus that generated frame-shift mutations (21).

All three cGAS mutant cell lines failed to activate IRF3 in response to HT-DNA transfection or herpes simplex virus (HSV-1; a double-stranded DNA virus) infection. As controls, these cells activated IRF3 normally in response to transfection with poly[I:C] or infection with Sendai virus, an RNA virus. The cGAS mutant cells were also defective in inducing CXCL10 in response to HT-DNA, but this defect was rescued by transfecting the cells with the mouse cGAS expression plasmid.

We chose cGAS mutant clone #18 and the parental L929 cells to investigate the role of cGAS in innate immune recognition of HIV infection. In L929 cells stably expressing an shRNA against TREX1, but not the control luciferase, HIV-GFP infection induced IRF3 dimerization and the production of IFNβ and CXCL10. In contrast, the L929 cGAS mutant cells failed to mount any detectable immune response to HIV infection even when TREX1 was depleted, demonstrating the essential role of cGAS in immune responses against HIV. The depletion of cGAS did not affect IFNβ or CXCL10 induction by Sendai virus.

We have previously shown that HEK293T cells do not express detectable levels of cGAS and STING and thus fail to activate IRF3 in response to DNA transfection or DNA virus infection (13). Consistent with an important role of cGAS and STING in retrovirus detection, HIV-GFP infection activated IRF3 and STAT1 in THP1 but not HEK293T cells. In contrast, Sendai virus activated IRF3 and STAT1 in both cell lines. To determine if HIV infection leads to the production of endogenous cGAMP in human cells, we prepared lysates from HIV-infected THP1 and HEK293T cells, heated the lysates at 95° C. to denature most proteins, which were removed by centrifugation (12). The supernatant that potentially contained cGAMP was delivered to THP1 cells that had been permeabilized with the bacterial toxin perfringolysin-O (PFO), and then IRF3 dimerization was assayed by native gel electrophoresis. The heat-resistant supernatant from HIV-infected THP1, but not HEK293T cells, contained the cGAMP activity that stimulated IRF3 activation in the recipient cells. Furthermore, inhibition of HIV reverse transcription by AZT, DDI (didanosine) or NVP blocked the generation of the cGAMP activity, whereas the HIV integrase inhibitor RAL had no effect. HIV-GFP infection in L929-shTrex1 cells also led to generation of the cGAMP activity, which was dependent on cGAS, Taken together, these results indicate that HIV infection induces the production of endogenous cGAMP in a manner that depends on cGAS and reverse transcription of HIV RNA to cDNA.

To test if HIV infection produces retroviral cDNA in the cytoplasm to activate cGAS, we infected HEK293T cells with HIV-GFP and prepared cytosolic extracts that were then incubated with purified cGAS protein in the presence of ATP and GTP. Cytosolic extracts from HIV-infected cells, but not from uninfected cells, were able to stimulate cGAS to produce the cGAMP activity that activated IRF3 in permeabilized THP1 cells. Treatment of HEK293T cells with AZT inhibited the generation of the cGAS stimulatory activity. Further analyses showed that the cytoplasm of HIV-infected cells contained the HIV Gag DNA and GFP protein, both of which were inhibited by AZT.

Quantitative measurement of cGAMP abundance by mass spectrometry using selective reaction monitoring (SRM) provided the direct evidence that cGAMP was produced in HIV-infected, but not mock-treated, THP1 cells. Tandem mass spectrometry of the endogenous cGAMP from HIV-infected THP1 cells revealed that it was identical to the cGAS product, 2'3'-cGAMP (15).

To test whether HIV infection in primary human immune cells leads to cGAMP production, we infected monocyte-derived macrophages (MDM) and monocyte-derived dendritic cells (MDDC) with the clinical HIV-1 isolate HW-BaL and HW-GFP, respectively. Previous research has shown that human macrophages and dendritic cells express SAMHD1, a nuclease that hydrolyzes dNTP, thereby inhibiting HIV reverse transcription. HW-2 and simian immunodeficiency virus (SIV) contain the protein Vpx, which targets SAMHD1 for ubiquitin-mediated proteasomal degradation, thus removing this host restriction factor. To facilitate HIV infections in human MDMs and MDDCs, we delivered the SIV Vpx into these cells using a virus-like particle (VLP) before HIV infection. In the presence of Vpx, infection of MDMs and MDDCs with HW-BaL and HIV-GFP, respectively, led to the generation of cGAMP activity. Quantitative mass spectrometry analysis further confirmed the production of 2'3'-cGAMP in HIV-infected MDDCs that expressed Vpx. The cGAMP activity was consistently observed in MDDCs and MDMs of additional human donors, and this activity was higher in the cells infected with HW than those treated with Vpx alone. These results demonstrate that HW infection in human macrophages and dendritic cells lead to the generation of cGAMP under conditions that are permissive to viral replication.

Finally, we tested whether cGAS is required for innate immune responses against other retroviruses by infecting L929 and L929-cGAS KO cell lines with murine leukemia virus (MLV) and SW. Similar to HW, MLV and SIV induced IFNβ and CXCL10 RNA in L929 cells depleted of endogenous TREX1, but such induction was completely abolished in the cGAS KO cells. In further support of an essential role of the cGAS-STING pathway in innate immune sensing of retroviruses, knockdown of cGAS or STING in Trex1 MEF cells strongly inhibited IFNβ induction by MLV and SIV.

Here we demonstrate that cGAS is essential for innate immune responses against HW, SIV and MLV, indicating that cGAS is a general innate immune sensor of retroviral DNA. Although HIV primarily infects human CD4 T cells, it can also enter macrophages and dendritic cells, normally without triggering an overt innate immune response by concealing the viral nucleic acids within the capsid and by limiting the accumulation of viral DNA through co-opting host factors such as TREX1 and SAMHD1 (8). The absence of a rigorous innate immune response to HIV in dendritic cells is thought to be a major factor that hampers productive T cell responses and vaccine development (7). Our finding that HIV and other retroviruses can induce the production of cGAMP through cGAS under permissive conditions indicates that cGAMP can be used to bypass the block of innate immune responses against HIV. As such, cGAMP provides a useful vaccine adjuvant for HIV and other pathogens that are adept at subverting the host innate immune system.

REFERENCES AND NOTES

1. A. Iwasaki, R. Medzhitov, Regulation of adaptive immunity by the innate immune system. *Science* 327, 291 (Jan. 15, 2010).
2. O. Takeuchi, S. Akira, Pattern recognition receptors and inflammation. *Cell* 140, 805 (Mar. 19, 2010).
3. P. C. Ronald, B. Beutler, Plant and animal sensors of conserved microbial signatures. *Science* 330, 1061 (Nov. 19, 2010).
4. R. Medzhitov, D. Littman, HIV immunology needs a new direction. *Nature* 455, 591 (Oct. 2, 2008).
5. N. Manel, D. R. Littman, Hiding in plain sight: how HIV evades innate immune responses. *Cell* 147, 271 (Oct. 14, 2011).
6. N. Manel et al., A cryptic sensor for HIV-1 activates antiviral innate immunity in dendritic cells. *Nature* 467, 214 (Sep. 9, 2010).
7. J. Luban, Innate immune sensing of HIV-1 by dendritic cells. *Cell host & microbe* 12, 408 (Oct. 18, 2012).
8. N. Yan, Z. J. Chen, Intrinsic antiviral immunity. *Nat Immunol* 13, 214 (2012).
9. N. Yan, A. D. Regalado-Magdos, B. Stiggelbout, M. A. Lee-Kirsch, J. Lieberman, The cytosolic exonuclease TREX1 inhibits the innate immune response to human immunodeficiency virus type 1. *Nature immunology* 11, 1005 (November, 2010).
10. D. B. Stetson, J. S. Ko, T. Heidmann, R. Medzhitov, Trex1 prevents cell-intrinsic initiation of autoimmunity. *Cell* 134, 587 (Aug. 22, 2008).
11. Y. J. Crow et al., Mutations in the gene encoding the 3'-5' DNA exonuclease TREX1 cause Aicardi-Goutieres syndrome at the AGS1 locus. *Nature genetics* 38, 917 (August, 2006).
12. J. Wu et al., Cyclic GMP-AMP is an endogenous second messenger in innate immune signaling by cytosolic DNA. *Science* 339, 826 (Feb. 15, 2013).
13. L. Sun, J. Wu, F. Du, X. Chen, Z. J. Chen, Cyclic GMP-AMP synthase is a cytosolic DNA sensor that activates the type I interferon pathway. *Science* 339, 786 (Feb. 15, 2013).
14. P. Gao et al., Cyclic [G(2',5')pA(3',5')p] Is the Metazoan Second Messenger Produced by DNA-Activated Cyclic GMP-AMP Synthase. *Cell* 153, 1094 (May 23, 2013).
15. X. Zhang et al., Cyclic GMP-AMP Containing Mixed Phosphodiester Linkages Is An Endogenous High-Affinity Ligand for STING. *Molecular cell*, (Jun. 3, 2013).
16. E. J. Diner et al., The Innate Immune DNA Sensor cGAS Produces a Noncanonical Cyclic Dinucleotide that Activates Human STING. *Cell Rep* 3, 1355 (May 30, 2013).
17. A. Ablasser et al., cGAS produces a 2'-5'-linked cyclic dinucleotide second messenger that activates STING. *Nature* 498, 380 (Jun. 20, 2013).
18. G. N. Barber, Cytoplasmic DNA innate immune pathways. *Immunological reviews* 243, 99 (September, 2011).
19. D. E. Levy, J. E. Darnell, Jr., Stats: transcriptional control and biological impact. *Nature reviews. Molecular cell biology* 3, 651 (September, 2002).
20. T. Cermak et al., Efficient design and assembly of custom TALEN and other TAL effector-based constructs for DNA targeting. *Nucleic Acids Res* 39, e82 (July, 2011).
21. Clone #18 has frame-shift mutations in all three chromosomes. In addition to frame-shifts, clone #36 harbored a 9-bp deletion in one chromosome that removed 3 amino acids (215-217) in the catalytic domain, whereas clone #94 had 12-bp deletion in one chromosome and 18-bp deletion in another that removed 4 (214-217) and 6 (212-217) amino acids in the catalytic domain, respectively.

Example 5

Pivotal Roles of cGAS-cGAMP Signaling in Antiviral Defense and Immune Adjuvant Effects Invasion of microbial DNA into the cytoplasm of animal cells triggers a cascade of host immune reactions that help clear the infection; however, self DNA in the cytoplasm can cause autoimmune diseases. Biochemical approaches led to the identification of cyclic GMP-AMP (cGAMP) synthase (cGAS) as a cytosolic DNA sensor that triggers innate immune responses. Here we show that cells from cGAS-deficient (cGas$^{-/-}$) mice, including fibroblasts, macrophages and dendritic cells, failed to produce type-I interferons and other cytokines in response to DNA transfection or DNA virus infection. cGas$^{-/-}$ mice were more susceptible to lethal infection with herpes simplex virus-1 (HSV1) than wild type mice. We also show that cGAMP is an adjuvant that boosts antigen-specific T cell activation and antibody production.

The detection of foreign DNA invasion is a fundamental mechanism of host defense. In mammalian cells, the presence of foreign or self DNA in the cytoplasm is a danger signal that triggers the host innate immune responses (1). Through biochemical studies, we have recently identified cyclic GMP-AMP (cGAMP) synthase (cGAS) as an innate immune sensor of cytosolic DNA that triggers the production of type-I interferons and other inflammatory cytokines (2, 3). cGAS binds to DNA independently of its sequence; this binding activates cGAS to catalyze the synthesis of a unique cGAMP isomer, which contains both 2'-5' and 3'-5' phosphodiester linkages (4-7). This molecule, termed 2'3'cGAMP, functions as a second messenger that binds and activates the adaptor protein STING (3, 7). STING then activates the protein kinases IKK and TBK1, which in turn activate the transcription factors NF-κB and IRF3 to induce interferons and cytokines (8).

To investigate the function of cGAS in vivo, we generated a cGas knockout mouse strain, in which the first exon is spliced into a LacZ cassette, thus abrogating the expression of the endogenous locus (9). The cGas$^{-/-}$ mice were born at the Mendelian ratio, and did not display any overt developmental abnormality. Quantitative reverse transcription PCR (q-RT-PCR) analyses of RNA from lung fibroblasts and bone marrow derived macrophages (BMDM) confirmed that the cGas$^{-/-}$ cells were defective in producing cGas RNA, whereas cGas cells produced intermediate levels of cGas RNA.

We obtained lung fibroblasts from WT, cGas$^{+/-}$ and cGAS$^{-/-}$ mice as well as the goldenticket (gt/gt) mouse, which has a point mutation that results in the loss of expression of STING (10). Transfection of different types of DNA, including herring testis DNA (HT-DNA), E. coli DNA and interferon stimulatory DNA (ISD; a 45 bp double-stranded DNA) (11), into the lung fibroblasts from WT and cGas$^{+/-}$ mice led to robust production of IFNβ protein, as measured by ELISA. In contrast, the cGas$^{-/-}$ and Sting$^{gt/gt}$ cells failed to produce any detectable level of IFNβ. Poly [I:C], a double-stranded RNA analogue known to induce IFNβ through the RIG-I like-receptor (RLR) pathway (12), induced IFNβ normally in the absence of cGas or Sting. Interestingly, poly[dA:dT], which was previously shown to induce type-I interferons through the RNA polymerase III-RIG-I-MAVS pathway (13, 14), induced IFNβ normally in the cGas$^{-/-}$ and Sting$^{gt/gt}$ cells. q-RT-PCR analyses further confirmed that cGAS is essential for IFNβ RNA induction by different types of synthetic or bacterial DNA, except poly[dA:dT]. Time course experiments show that IFNβ induction by ISD was completely abolished in cGas$^{-/-}$ lung fibroblasts even at early time points (2-8 hr) after the DNA transfection, indicating that cGAS is indispensable for IFNβ induction by cytosolic DNA.

To measure cGAMP production in WT and cGas$^{-/-}$ cells, we performed a bioassay that measures the cGAMP activity in cytoplasmic extracts from ISD-transfected cells. The extracts were heated at 95° C. to denature most proteins, which were removed by centrifugation. The supernatants that might contain cGAMP were delivered to the human monocytic cell line THP1, which had been permeabilized with the bacterial toxin perfringolysin-O (PFO). Dimerization of IRF3, a hallmark of its activation, was then measured by native gel electrophoresis. This assay showed that the extracts of ISD-transfected lung fibroblasts from WT but not cGas$^{-/-}$ mice contained the cGAMP activity, demonstrating that cGAS has a non-redundant role in catalyzing cGAMP synthesis in these cells in response to cytosolic DNA.

Next, we infected the lung fibroblasts with the DNA viruses herpes simplex virus-1 (HSV1), vaccinia virus (VACV) and a mutant strain of HSV1 called d109, which has a deletion of viral proteins such as ICP0 that is known to antagonize immune responses (15). IFNβ induction by each of these viruses was largely abolished in cGas$^{-/-}$ and Sting$^{gt/gt}$ cells, and partially inhibited in cGas$^{+/-}$ cells. In contrast, IFNβ induction by Sendai virus, an RNA virus known to activate the RIG-I pathway, was not affected by the deficiency in cGas or Sting. Delivery of cGAMP into the cytoplasm rescued IFNβ induction in cGas$^{-/-}$ cells but not Sting$^{gt/gt}$ cells. Similarly, induction of the chemokine CXCL10 by the DNA viruses was dependent on cGas and Sting. Measurement of IRF3 dimerization showed that cGas$^{-/-}$ cells failed to activate IRF3 in response to transfection of HT-DNA or infection by WT HSV1 or the HSV1 strain 7134, which also lacks the interferon antagonist ICP0 (16). The cGas deficiency did not impair IRF3 activation by Sendai virus. Thus, cGAS is required for IRF3 activation and cytokine induction by DNA viruses but not RNA viruses in mouse lung fibroblasts.

BMDM from cGas$^{-/-}$ and Sting$^{gt/gt}$ mice were defective in producing IFNβ in response to transfection with HT-DNA or ISD. Similarly, IFNβ induction by VACV and the HSV1 strains d109 and 7134 was largely abolished in cGas$^{-/-}$ and Sting$^{gt/gt}$ BMDM. However, IFNβ induction by WT HSV1 was severely but not completely blocked in either cGas$^{-/-}$ or Sting$^{gt/gt}$ BMDM, indicating that these cells possess another pathway that could partially compensate for the loss of the cGAS-STING pathway to detect WT HSV1 infection. The loss of cGAS or STING in BMDM did not affect IFNβ induction by Sendai virus. Kinetic experiments show that IFNβ induction by ISD and HSV1-d109 was abolished in cGas$^{-/-}$ BMDM throughout the time course of stimulation. Similarly to IFNβ, the induction of TNFα by HT-DNA or ISD was abolished in cGas$^{-/-}$ or Sting$^{gt/gt}$ BMDM. q-RT-PCR analyses showed that the induction of IFNβ, interleukin-6 (IL6) and CXCL10 RNA by transfection of HT-DNA or ISD or infection with HSV1-d109 was completely dependent on cGas and Sting. In contrast, the RNA levels of these cytokines induced by poly[I:C] or Sendai virus were not affected by the deficiency in cGas or Sting.

We obtained conventional dendritic cells (cDC) and plasmacytoid DCs (pDC) by culturing bone marrows in conditioned media containing GM-CSF and Flt3 ligand (Flt3L), respectively. The GM-CSF DCs, which contains largely cDC, from the cGas$^{-/-}$ and Sting$^{gt/gt}$ mice failed to induce IFNα or IFNβ in response to transfection of HT-DNA or ISD. The loss of cGAS or STING in GM-CSF DCs abolished IFNβ induction by HSV1-d109 and VACV, and partially inhibited IFNβ induction by WT HSV1. In contrast, the deficiency in cGAS or STING did not impair IFNα or IFNβ induction by Sendai virus. q-RT-PCR experiments further confirmed that cGAS and STING were essential for the induction of IFNβ, IL6 and CXCL10 RNA by transfection with HT-DNA or ISD or infection with HSV1-d109, whereas the induction of these cytokines by poly[I:C] or Sendai virus was independent of cGAS or STING.

pDCs are known to express TLR9 that is responsible for the induction of type-I interferons by synthetic CpG DNA containing phosphorothioate bonds (17). When the CpG DNA was used to stimulate Flt3L-DCs, which contains largely pDCs, in the presence or absence of liposome (lipofectamine 2000), it induced robust production of IFNα and IFNβ even in the cGas$^{-/-}$ and Sting$^{gt/gt}$ cells. In contrast, other forms of DNA, including ISD, poly[dA:dT] and genomic DNA from E. coli and Vibrio cholerae, induced IFNα in Flt3L-DCs only in the presence of liposome, and this induction by each DNA was abolished in the absence of cGAS or STING. The strong dependency of IFNα induction by poly[dA:dT] on cGAS and STING in pDCs indicates that the cGAS-STING pathway, but not the Pol-III-RIG-I pathway, plays a major role in sensing the DNA in these cells. The Flt3L-DC from the cGas$^{-/-}$ and Sting$^{gt/gt}$ mice induced IFNα and IFNβ in response to infection by Sendai virus, but not HSV1. Together, these results demonstrate that cGAS is responsible for detecting natural DNA (e.g., bacterial DNA) and DNA virus infections in dendritic cells.

To determine the role of cGAS in immune defense against DNA viruses in vivo, we infected WT and cGas$^{-/-}$ mice with HSV1 via the intravenous (i.v) route. ELISA analyses showed that the sera of WT mice contained elevated levels of IFNα and IFNβ, which peaked at 8 and 4 hours, respectively, after HSV1 infection (1×10$^7$ pfu/mouse). The levels of IFNα and IFNβ were severely attenuated in the cGas$^{-/-}$ mice infected with the same infectious dose of HSV1. In an independent experiment in which the mice were monitored for their survival after infection with HSV1 at the infectious dose of 1×10$^6$ pfu/mouse, four out of the five cGas$^{-/-}$ mice developed ataxia and paralysis in 3 days after the virus infection and died a few hours after these symptoms appeared. The fifth cGas$^{-/-}$ mouse died on day 4 after infection. Three out of five WT mice developed these symptoms on day 6 and died shortly afterwards. When the brains of WT and cGas$^{-/-}$ mice were extracted to measure viral titers on day 3 after infection, high levels of HSV1 were detected in all five cGas$^{-/-}$ mice, whereas none of the WT mice had detectable levels of HSV1 in the brains. Similar survival curves were observed and similar viral titers in the brains were detected in independent experiments where the infectious dose of HSV1 was increased to 1×10$^7$ pfu per mouse. The susceptibility of cGas$^{-/-}$ mice to HSV1 infection was similar to that of Stinegt mice, which also had marked reduction of IFNα and IFNβ in the sera, and died within 3-4 days after HSV1 infection (18).

Our results that cGAS is essential for the induction of type-I interferons by cytosolic DNA in multiple cell types, including antigen presenting cells, indicate that the cGAS product, 2'3'cGAMP, can be used to substitute for the immune stimulatory effect of DNA, including the adjuvant effect of DNA vaccines (19). To ascertain the adjuvant effect of 2'3'cGAMP, we injected the model protein antigen ovalbumin (OVA) in the absence or presence of 2'3'cGAMP into WT or Sting$^{gt/gt}$ mice via the intramuscular (i.m) route. The mice were boosted once on day 10 with the same antigen formulation. ELISA analyses showed that 2'3'cGAMP strongly enhanced the production of OVA-specific antibodies on day 17 in the WT, but not Sting$^{gt/gt}$ mice. This adjuvant effect of 2'3'cGAMP was also not observed in type-I interferon receptor deficient mice (Ifnar$^{-/-}$). To investigate the effect of 2'3'cGAMP on T cell activation, splenic leukocytes isolated from the WT mice, which had been immunized with OVA or OVA+2'3'cGAMP for 7 days, were cultured with an OVA peptide known to stimulate CD4 T cells through the MHC class II molecule I-A$^b$ or another OVA peptide that stimulates CD8 T cells through the MHC class I molecule H-2K$^b$. Both CD4 and CD8 T cells from the mice immunized with OVA+2'3'cGAMP, but not OVA alone, produced elevated levels of IFNγ and IL-2 after stimulation with the cognate peptides. Flow cytometry analysis using a tetramer composed of an OVA peptide in complex with H-2K$^b$ showed a marked increase in the percentage of the tetramer-positive CD8 T cells in the mice immunized with OVA+2'3'cGAMP, indicating that 2'3'cGAMP stimulated the expansion of CD8 T cells bearing the OVA-specific T cell receptor. Taken together, these results indicate that 2'3'cGAMP functions as an immune adjuvant to stimulate antigen-specific T cell and B cell responses.

Here we provide evidence that cGAS is essential for the induction of type-I interferons and other inflammatory cytokines by DNA transfection and DNA virus infection. With the exception of poly[dA:dT] and CpG DNA, most DNA molecules, especially those found in nature (e.g., bacterial and viral DNA), stimulate type-I interferons exclusively through the cGAS-cGAMP-STING pathway. In multiple cell types, including fibroblasts, macrophages and dendritic cells, the induction of type-I interferons by vaccinia viruses and several strains of HSV1 is completely dependent on cGAS and STING. Notably, however, IFNβ induction by wild type HSV1 is severely but not completely abolished in BMDM and GM-CSF DCs from cGas$^{-/-}$ or Sting$^{gt/gt}$ mice. Other putative DNA sensors, such as IFI16 or DDX41, may also be involved in this residual induction of IFNβ by WT HSV1 (20, 21). In the case of cGAS, the phenotypes of cGas$^{-/-}$ mice are strikingly similar to those of Sting$^{-/-}$ mice (this study and ref. 18). These results, together with our biochemical data showing that cGAS is a cytosolic enzyme activated by its binding to generic DNA (2, 3), formally demonstrate that cGAS is a non-redundant and general cytosolic DNA sensor that activates STING.

We show that 2'3'cGAMP is an effective adjuvant that boosts the production of antigen-specific antibodies and T cell responses. Although the bacterial second messengers cyclic di-GMP and cyclic di-AMP are being developed as potential vaccine adjuvants (22), 2'3'cGAMP is a much more potent ligand of STING than any of the bacterial cyclic di-nucleotides (7). Thus, 2'3'cGAMP provides a useful adjuvant for next generation vaccines to prevent or treat human diseases, including infectious diseases and cancer.

REFERENCES AND NOTES

1. L. A. O'Neill, Immunology. Sensing the dark side of DNA. *Science* 339, 763 (Feb. 15, 2013).
2. L. Sun, J. Wu, F. Du, X. Chen, Z. J. Chen, Cyclic GMP-AMP synthase is a cytosolic DNA sensor that activates the type I interferon pathway. *Science* 339, 786 (Feb. 15, 2013).
3. J. Wu et al., Cyclic GMP-AMP is an endogenous second messenger in innate immune signaling by cytosolic DNA. *Science* 339, 826 (Feb. 15, 2013).
4. A. Ablasser et al., cGAS produces a 2'-5'-linked cyclic dinucleotide second messenger that activates STING. *Nature* 498, 380 (Jun. 20, 2013).
5. E. J. Diner et al., The Innate Immune DNA Sensor cGAS Produces a Noncanonical Cyclic Dinucleotide that Activates Human STING. *Cell Rep* 3, 1355 (May 30, 2013).
6. P. Gao et al., Cyclic [G(2',5')pA(3',5')p] Is the Metazoan Second Messenger Produced by DNA-Activated Cyclic GMP-AMP Synthase. *Cell* 153, 1094 (May 23, 2013).
7. X. Zhang et al., Cyclic GMP-AMP Containing Mixed Phosphodiester Linkages Is An Endogenous High-Affinity Ligand for STING. *Molecular cell*, (Jun. 3, 2013).
8. H. Ishikawa, G. N. Barber, The STING pathway and regulation of innate immune signaling in response to DNA pathogens. *Cellular and molecular life sciences: CMLS* 68, 1157 (April, 2011).
9. cGas$^{-/-}$ mice were generated by in vitro fertilization using sperms harboring a targeted insertion at the cGas/Mb21d1 locus.
10. J. D. Sauer et al., The N-ethyl-N-nitrosourea-induced Goldenticket mouse mutant reveals an essential function of Sting in the in vivo interferon response to Listeria monocytogenes and cyclic dinucleotides. *Infect Immun* 79, 688 (February, 2011).
11. D. B. Stetson, R. Medzhitov, Recognition of cytosolic DNA activates an IRF3-dependent innate immune response. *Immunity* 24, 93 (January, 2006).

12. M. Yoneyama et al., The RNA helicase RIG-I has an essential function in double-stranded RNA-induced innate antiviral responses. *Nat Immunol* 5, 730 (July, 2004).
13. A. Ablasser et al., RIG-I-dependent sensing of poly(dA:dT) through the induction of an RNA polymerase III-transcribed RNA intermediate. *Nat Immunol*, (Jul. 16, 2009).
14. Y. H. Chiu, J. B. Macmillan, Z. J. Chen, RNA polymerase III detects cytosolic DNA and induces type I interferons through the RIG-I pathway. *Cell* 138, 576 (Aug. 7, 2009).
15. L. A. Samaniego, L. Neiderhiser, N. A. DeLuca, Persistence and expression of the herpes simplex virus genome in the absence of immediate-early proteins. *Journal of virology* 72, 3307 (April, 1998).
16. G. T. Melroe, N. A. DeLuca, D. M. Knipe, Herpes simplex virus 1 has multiple mechanisms for blocking virus-induced interferon production. *Journal of virology* 78, 8411 (August, 2004).
17. O. Takeuchi, S. Akira, Pattern recognition receptors and inflammation. *Cell* 140, 805 (Mar. 19, 2010).
18. H. Ishikawa, Z. Ma, G. N. Barber, STING regulates intracellular DNA-mediated, type I interferon-dependent innate immunity. *Nature* 461, 788 (Oct. 8, 2009).
19. C. J. Desmet, K. J. Ishii, Nucleic acid sensing at the interface between innate and adaptive immunity in vaccination. *Nature reviews. Immunology* 12, 479 (July, 2012).
20. Z. Zhang et al., The helicase DDX41 senses intracellular DNA mediated by the adaptor STING in dendritic cells. *Nature immunology* 12, 959 (October, 2011).
21. L. Unterholzner et al., IFI16 is an innate immune sensor for intracellular DNA. *Nature immunology* 11, 997 (November, 2010).
22. W. Chen, R. Kuolee, H. Yan, The potential of 3',5'-cyclic diguanylic acid (c-di-GMP) as an effective vaccine adjuvant. *Vaccine* 28, 3080 (Apr. 19, 2010).

What is claimed is:

1. An injectable pharmaceutical formulation comprising a pharmaceutically acceptable carrier containing a cyclic dinucleotide comprising a 5'-monophosphate nucleotide comprising a guanine moiety, and a 5'-monophosphate nucleotide comprising an adenine moiety, wherein the cyclic dinucleotide has a phosphodiester bond between the 2'-OH of the nucleotide comprising the guanine moiety and the 5'-phosphate of the nucleotide comprising the adenine moiety, and a phosphodiester bond between the 3'-OH of the nucleotide comprising the adenine moiety and the 5'-phosphate of the nucleotide comprising the guanine moiety.

2. The pharmaceutical formulation of claim 1, wherein the cyclic dinucleotide activates the STING protein.

3. The pharmaceutical formulation of claim 1, wherein the cyclic dinucleotide is able to bind to the STING protein.

4. The pharmaceutical formulation of claim 3, wherein the cyclic dinucleotide is able to bind to the Y240 residue of the STING protein.

5. The pharmaceutical formulation of claim 3, wherein the cyclic dinucleotide is able to bind to the N242 residue of the STING protein.

6. The pharmaceutical formulation of claim 3, wherein the cyclic dinucleotide is able to bind to the Y240 and N242 residues of the STING protein.

7. The pharmaceutical formulation of claim 1, wherein the formulation is free of other cyclic dinucleotides.

8. A method of inducing or promoting an immune response comprising administering by injection to a mammal in need thereof an effective amount of the pharmaceutical formulation of claim 1.

9. The method of claim 8, wherein the cyclic dinucleotide activates the STING protein.

10. The method of claim 8, wherein the cyclic dinucleotide is able to bind to the STING protein.

11. The method of claim 10, wherein the cyclic dinucleotide is able to bind to the Y240 residue of the STING protein.

12. The method of claim 10, wherein the cyclic dinucleotide is able to bind to the N242 residue of the STING protein.

13. The method of claim 10, wherein the cyclic dinucleotide is able to bind to the Y240 and N242 residues of the STING protein.

14. The method of claim 8, further comprising administering an immunogen to the subject.

15. The method of claim 8, wherein the immunogen is a vaccine.

* * * * *